(12) United States Patent
Thorne

(10) Patent No.: US 7,297,818 B2
(45) Date of Patent: Nov. 20, 2007

(54) ADAMANTANE DERIVATIVES

(75) Inventor: Philip Thorne, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/529,746

(22) Filed: Sep. 29, 2006

(65) Prior Publication Data

US 2007/0082957 A1    Apr. 12, 2007

Related U.S. Application Data

(63) Continuation of application No. 10/813,426, filed on Mar. 31, 2004, now Pat. No. 7,132,457, which is a continuation of application No. 10/149,549, filed as application No. PCT/SE00/02505 on Dec. 12, 2000, now Pat. No. 6,881,754.

(30) Foreign Application Priority Data

Dec. 17, 1999  (SE) .................... 9904651
Jun. 27, 2000  (GB) .................. 0015744.6
Jul. 22, 2000  (GB) .................. 0017942.4

(51) Int. Cl.
*C07C 233/65* (2006.01)
(52) U.S. Cl. ..................... 564/169; 564/183
(58) Field of Classification Search ........... 564/169, 564/183
See application file for complete search history.

(56) References Cited

U.S. PATENT DOCUMENTS

| | | |
|---|---|---|
| 3,029,241 A | 4/1962 | Fancher et al. |
| 3,464,998 A | 9/1969 | Krimmel et al. |
| 3,732,305 A | 5/1973 | Bauer et al. |
| 3,789,072 A | 1/1974 | Bernstein |
| 6,201,024 B1 | 3/2001 | Baxter et al. |
| 6,242,470 B1 | 6/2001 | Baxter et al. |
| 6,258,838 B1 | 7/2001 | Baxter et al. |
| 6,303,659 B2 | 10/2001 | Baxter et al. |
| 6,492,355 B1 | 12/2002 | Alcaraz et al. |
| 6,555,541 B1 | 4/2003 | Furber et al. |
| 6,720,452 B2 | 4/2004 | Alcaraz et al. |
| 6,881,754 B2 | 4/2005 | Alcaraz et al. |
| 6,949,539 B2 | 9/2005 | Alcaraz et al. |
| 7,129,246 B2 | 10/2006 | Alcaraz et al. |
| 7,132,457 B2 | 11/2006 | Alcaraz et al. |

FOREIGN PATENT DOCUMENTS

| | | |
|---|---|---|
| EP | 0074768 | 3/1983 |
| EP | 0395093 A1 | 10/1990 |
| EP | 0564924 A2 | 10/1993 |
| EP | 0582164 A1 | 2/1994 |
| FR | 2346011 | 10/1977 |
| WO | WO95/04720 | 2/1995 |
| WO | WO95/30647 | 11/1995 |
| WO | WO95/32949 | 12/1995 |
| WO | WO96/13262 | 5/1996 |
| WO | WO97/32882 | 9/1997 |
| WO | WO99/29660 A1 | 6/1999 |
| WO | WO99/29661 A1 | 6/1999 |
| WO | WO99/29686 | 6/1999 |
| WO | WO99/31096 | 6/1999 |
| WO | WO99/59582 | 11/1999 |
| WO | WO 00/61569 | 10/2000 |
| WO | WO 00/71529 A1 | 11/2000 |
| WO | WO 01/42194 A1 | 6/2001 |
| WO | WO 01/44213 A1 | 6/2001 |
| WO | WO 01/46200 A1 | 6/2001 |
| WO | WO 01/94338 | 12/2001 |
| WO | WO 03/041707 | 5/2003 |
| WO | WO 03/080579 | 10/2003 |

(Continued)

OTHER PUBLICATIONS

Billotte, "Synthesis of C-Substituted Cyclic Amines Using Azacycloalkyl Organozinc Reagents", Syn. Lett., 1998, pp. 379-380.

(Continued)

*Primary Examiner*—Shailendra Kumar
(74) *Attorney, Agent, or Firm*—Morgan Lewis & Bockius LLP

(57) ABSTRACT

The invention provides adamantane derivatives of formula (I), a process for their preparation, pharmaceutical compositions containing them, a process for preparing the pharmaceutical compositions, and their use in therapy. In formula (I) D represents $CH_2$ or $CH_2CH_2$, E represents C(O)NH or NHC(O) and $R^3$ represents a group of formula (II)

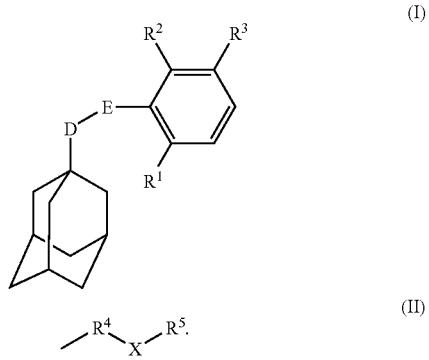

1 Claim, No Drawings

FOREIGN PATENT DOCUMENTS

| WO | WO 2004/074224 | 9/2004 |
| WO | WO 2005/025571 | 3/2005 |
| WO | WO 2006/025783 | 3/2006 |
| WO | WO 2006/059945 | 6/2006 |

OTHER PUBLICATIONS

Chemical Abstracts, vol. 57 (1962), Shin Hayao et al., "New sedative and hypotensive phenylpiperazine amides", The Abstract No. 3443i, J. Org. Chem. 1961, 26, 3414-3419.

Chemical Abstracts, vol. 82, No. 3, Jan. 20, 1975, No et al., "Tetrakis(I-adamantyacetoxy)silane in organic synthesis", Abstract No. 16510v. p. 469, Zh. Obshch. Kim. 1974, 44 (10), 2359.

Chemical Abstracts, vol. 84, No. 9, Mar. 1, 1976, p. 527, The Abstract No. 59466u, JP 75108264A (Maruyama, Isamu et al.) Aug. 26, 1975.

Chemical Abstracts, vol. 86, No. 17, Apr. 25, 1977, Danilenko et al., "Synthesis and biological activity of adamantane derivatives. V. Virus-inhibiting effect of arylamides of adamantanecarboxylic acids", p. 505, Abstract No. 120855e, Khim-Farmm.Zh. 1976, 10(7), pp. 60-62.

Claxton et al., "2,3,4,5-Tetrahydropyridine", Org. Synth. 1977, vol. 56, pp. 118-122.

Liverton et al., "Design and Synthesis of Potent, Selective, and Orally Bioavailable Tetrasubstituted Imidazole Inhibitors of p38 Mitogen-Activated Protein Kinase", J. Med. Chem., 1999, vol. 42, pp. 2180-2190.

Narayanan, "Adamantyl Analogs of 2-(3-Dimethylaminopropylthio)cinnamanilide", Journal of Medicinal Chemistry, vol. 15, No. 11, pp. 1180-1182, 1972.

Nomura et al., "Synthesis of Cyclic Imines Having Conjugated Exocyclic Double Bond", Bull. Chem. Soc. Jpn., 1983, vol. 56, p. 3199-3120.

Palucki et al., "Palladium-Catalyzed Intermolecular Carbon-Oxygen Bond Formation: A New Synthesis of Aryl Ethers", J. Am. Chem., 1997, vol. 119, pp. 3395-3396.

Smith et al., "Solid and Solution Phase Organic Syntheses of Oligomeric Thioureas", J. Org. Chem, 1996, vol. 61, pp. 8811-8818.

STN International, File CAPLUS, CAPLUS accession No. 1974:26871, Document No. 80:28671, Danilenko et al., "Synthesis and biological activity of adamantane derivatives. II. N-(1-Adamantoyl)anthranilic acids", Kim.-Farm.Zh., 1973, 7(10), pp. 15-17.

STN International, File CAPLUS, CAPLUS accession No. 1975:592744, Document No. 83:192744, Kreutzberger et al., "Antiviral agents. 4. Aromatically substituted carbonic acid amide structure in potentially virustatic compounds", Arzneim.-Forsch., 1975, 25(7) 994-997.

STN International, File CAPLUS, CAPLUS accession No. 1977:89560, Document No. 86:89560, Danilenko, G.I., et al., "Synthesis and biological activity of adamatane derivatives. VI. Antiinflammatory action of adamantylamides of pyridinecarboxylicacids"; Khim.-Famr.zh. (1976, 10(8), pp. 51-53.

STN International, File CAPLUS, CAPLUS accession No. 1991:656226, Document No. 115:256226, Kowa K.K., "Preparation of piperazine derivatives as antiarrhythmics", & JP, A2, 19910617.

STN International, File CAPLUS, CAPLUS accession No. 1995:324637, Document No. 122:105919, Kyowa Hakko Kogyo KK: Preparation of quinazolinylpiperazineacetamide derivatives; & JP A2, 06247942, 19940906.

STN International, File CAPLUS, CAPLUS accession No. 1996:344490, Document No. 125:115117, Kalindjian et al., "The Synthesis of a radioligand with high potency and selectivity for CCKB/gastrain receptors", Bioorg. Med. Chem. Lett. 1996, 6(10), pp. 1171-1174.

STN International, File CAPLUS, CAPLUS accession No. 1997:390174, Document No. 127:95591, Gibson et al., "Incorporation of conformationally constrained phenylalanine derivatives Tic, Sic, Hic and Nic into a cholecystokinin-b/gastrin receptor antagonist", Bioorg. Med. Chem. Lett., 1997, 7(10), pp. 1289-1292.

STN International, File CAPLUS, CAPLUS accession No. 1968:402562, Document No. 69:2562, Sasaki et al., "Synthesis of adamantane derivatives II. Preparation of some derivatives from adamantylacetric acid", Bull. Chem. Soc. Jap., 1968, 41(1), pp. 238-240.

STN International, File CAPLUS, CAPLUS accession No.1975:3853, Document No. 82:3853, Kreutzberger et al., "Antiviral agents. 3. Aliphatic acid amide grouping as partial structure in virustatics", Arch. Pham., 1974, 307(10), pp. 766-774.

Syamala et al., "Modification of Photochemical Reactivity by Cyclodextrin Complexation: Product Selectivity in Photo-Fries Rearrangement", Tetrahedron, vol. 44, No. 23, 1998, pp. 7234-7242.

Tsunoda et al., "1,1'-(Azodicarbonyl)dipiperidine-Tributylphosphine, A New Reagent System for Mitsunobu Reaction", Tetrahedron Letters, vol. 34, No. 10, 1993, pp. 1639-1642.

Wolfe et al., "An Improved Catalyst System for Aromatic Carbon—Nitrogen Bond Formation: The Possible Involvement of Bis(Phosphine) Palladium Complexes as Key Intermediates", J. Am. Chem. Soc., 1996, vol. 118, pp. 7215-7216.

Zeng et al., "Design of New Topoisomerase II Inhibitors Based upon a Quinobenzoxazine Self-Assembly Model", J. Med. Chem., vol. 41, pp. 4273-4278, 1998.

ADAMANTANE DERIVATIVES

This is a Continuation of application Ser. No. 10/813,426, filed Mar. 31, 2004, (now U.S. Pat. No. 7,132,457), which is a continuation of application Ser. No. 10/149,549, filed Jun. 12, 2002 (now U.S. Pat. No. 6,881,754), which is a U.S. National Stage of PCT/SE00/02505 filed Dec. 12, 2000.

The present invention relates to adamantane derivatives, a process for their preparation, pharmaceutical compositions containing them, a process for preparing the pharmaceutical compositions, and their use in therapy.

The $P2X_7$ receptor (previously known as P2Z receptor), which is a ligand-gated ion channel, is present on a variety of cell types, largely those known to be involved in the inflammatory/immune process, specifically, macrophages, mast cells and lymphocytes (T and B). Activation of the $P2X_7$ receptor by extracellular nucleotides, in particular adenosine triphosphate, leads to the release of interleukin-1β (IL-1β) and giant cell formation (macrophages/microglial cells), degranulation (mast cells) and L-selectin shedding (lymphocytes). $P2X_7$ receptors are also located on antigen-presenting cells (APC), keratinocytes, salivary acinar cells (parotid cells), hepatocytes, erythrocytes, erythroleukaemic cells, monocytes, fibroblasts, bone marrow cells, neurones and renal mesangial cells.

It would be desirable to make compounds effective as $P2X_7$ receptor antagonists for use in the treatment of inflammatory, immune or cardiovascular diseases, in the aetiologies of which the $P2X_7$ receptor may play a role.

In accordance with the present invention, there is therefore provided a compound of general formula

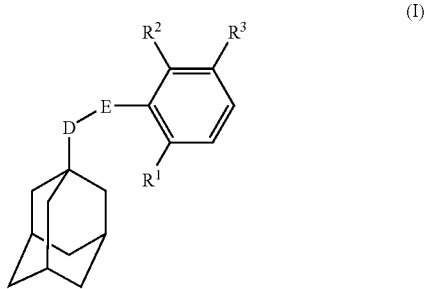

where D represents $CH_2$ or $CH_2CH_2$, preferably $CH_2$;
E represents C(O)NH or, preferably, NHC(O);
$R^1$ and $R^2$ each independently represent hydrogen, halogen (e.g. fluorine, chlorine, bromine or iodine), amino ($NH_2$), nitro ($NO_2$), $C_1$-$C_6$ alkyl or trifluoromethyl, but $R^1$ and $R^2$ may not both simultaneously represent hydrogen;
$R^3$ represents a group of formula

$R^4$ represents a $C_1$-$C_6$ alkyl group;
X represents an oxygen or sulphur atom or a group $NR^{13}$, SO or $SO_2$;
$R^5$ represents hydrogen, or $R^5$ represents $C_1$-$C_6$ alkyl or $C_2$-$C_6$ alkenyl, each of which may be optionally substituted by at least one substituent selected from halogen, hydroxyl, (di)-$C_1$-$C_6$-alkylamino, —Y—$R^6$,

a 5- or 6-membered heteroaromatic ring comprising from 1 to 4 heteroatoms independently selected from nitrogen, oxygen and sulphur which heteroaromatic ring may itself be optionally substituted by at least one substituent selected from halogen, hydroxyl and $C_1$-$C_6$ alkyl;
Y represents an oxygen or sulphur atom or a group NH, SO or $SO_2$;
$R^6$ represents a group —$R^7$Z where $R^7$ represents a $C_2$-$C_6$ alkyl group and Z represents an —OH, —$CO_2H$, —$NR^8R^9$, —C(O)$NR^{10}R^{11}$ or —N($R^{12}$)C(O)-$C_1$-$C_6$ alkyl group, and, in the case where Y represents an oxygen or sulphur atom or a group NH, $R^6$ additionally represents hydrogen, $C_1$-$C_6$ alkyl, $C_1$-$C_6$ alkylcarbonyl, $C_1$-$C_6$ alkoxycarbonyl, —C(O)$NR^{14}R^{15}$, —$CH_2OC(O)R^{16}$, —CH$^2$OC(O)$OR^{17}$ or —C(O)OCH$_2OR^{18}$;
$R^8$, $R^9$, $R^{10}$, $R^{11}$ and $R^{12}$ each independently represent a hydrogen atom or a $C_1$-$C_6$ alkyl group;
$R^{13}$ represents hydrogen, $C_3$-$C_8$ cycloalkyl, $C_3$-$C_8$ cycloalkylmethyl, or $R^{13}$ represents a $C_1$-$C_6$ alkyl group optionally substituted by at least one substituent selected from hydroxyl and $C_1$-$C_6$ alkoxy; and
$R^{14}$, $R^{15}$, $R^{16}$, $R^{17}$ and $R^{18}$ each independently represent a $C_1$-$C_6$ alkyl group;
with the proviso that when E is C(O)NH, X is O, NH or N($C_1$-$C_6$ alkyl), then $R^5$ is other than a hydrogen atom or an unsubstituted $C_1$-$C_6$ alkyl group;
or a pharmaceutically acceptable salt or solvate thereof.

In the context of the present specification, unless otherwise indicated, an alkyl substituent or alkyl moiety in a substituent group may be linear or branched. In the present invention, an alkyl group or moiety may contain up to 6 carbon atoms, examples of whcih include methyl, ethyl, n-propyl, isopropyl, n-butyl, isobutyl, t-butyl, n-pentyl and n-hexyl. A $C_2$-$C_6$ alkenyl group may be linear or branched. In a di-$C_1$-$C_6$-alkylamino group, the alkyl moieties may be the same or different.

In one embodiment of the invention, when E represents C(O)NH, then X is S, SO or $SO_2$.

In another embodiment of the invention, when E represents NHC(O), then X is O or $NR^{13}$.

Preferably, $R^1$ and $R^2$ each independently represent a hydrogen or halogen atom, or an amino, nitro, $C_1$-$C_4$ alkyl or trifluoromethyl group (but $R^1$ and $R^2$ may not both simultaneously represent a hydrogen atom).

More preferably, $R^1$ and $R^2$ each independently represent a hydrogen, chlorine or bromine atom, or an amino, nitro, $C_1$-$C_3$ alkyl or trifluoromethyl group (but $R^1$ and $R^2$ may not both simultaneously represent a hydrogen atom).

Most preferably, $R^1$ and $R^2$ each independently represent a hydrogen or chlorine atom (but $R^1$ and $R^2$ may not both simultaneously represent a hydrogen atom).

$R^4$ represents a $C_1$-$C_6$ alkyl group, for example a linear $C_1$-$C_6$ alkyl group such as $CH_2$, $(CH_2)_2$, $(CH_2)_3$ or $(CH_2)_4$.

Preferably X represents an oxygen atom or, especially, a group $NR^{13}$.

$R^5$ represents hydrogen, or $R^5$ represents $C_1$-$C_6$ alkyl or $C_2$-$C_6$ alkenyl (e.g. ethenyl or —$CH_2CH$=$CH_2$), each of which may be optionally substituted by at least one substituent, e.g. one, two or three substituents independently selected from halogen (e.g. fluorine, chlorine, bromine or iodine), hydroxyl, (di)-$C_1$-$C_6$-alkylamino (e.g. methylamino, ethylamino, dimethylamino or diethylamino), —Y—$R^6$,

a 5- or 6-membered heteroaromatic ring comprising 1, 2, 3 or 4 heteroatoms independently selected from nitrogen, oxygen and sulphur which heteroaromatic ring may itself be optionally substituted by at least one substituent, e.g. one or two substituents independently selected from halogen (e.g. fluorine, chlorine, bromine or iodine), hydroxyl and $C_1$-$C_6$, preferably $C_1$-$C_4$, alkyl, e.g., imidazolyl (such as imidazol-4-yl or imidazol-4-yl), 1-methylimidazolyl (such as 1-methylimidazol-4-yl), 2,3,5-triazolyl and 2,3,4,5-tetrazolyl.

Preferred compounds are those in which $R^5$ represents an optionally substituted $C_1$-$C_6$ alkyl group. A preferred optional substituent is —Y—$R^6$.

When Y represents SO or $SO_2$, $R^6$ represents a group —$R^7Z$ where $R^7$ represents a $C_2$-$C_6$ alkyl group and Z represents an —OH, —$CO_2H$, —$NR^8R^9$, —C(O)$NR^{10}R^{11}$ or —N($R^{12}$)C(O)—$C_1$-$C_6$ alkyl group.

When Y represents an oxygen or sulphur atom or a group NH, $R^6$ may represent a group —$R^7Z$ as defined above (particularly —$(CH_2)_2OH$ or —$(CH_2)_3OH$), or $R^6$ may represent hydrogen, $C_1$-$C_6$ alkyl (e.g. methyl, ethyl, n-propyl, isopropyl or t-butyl), $C_1$-$C_6$ alkylcarbonyl (e.g. methylcarbonyl, ethylcarbonyl, n-propylcarbonyl or t-butylcarbonyl), $C_1$-$C_6$ alkoxycarbonyl (e.g. methoxycarbonyl, ethoxycarbonyl, n-propoxycarbonyl or t-butoxycarbonyl), —C(O)$NR^{14}R^{15}$, —$CH_2OC(O)R^{16}$, —$CH_2OC(O)OR^{17}$ or —C(O)O$CH_2OR^{18}$.

Y is preferably an oxygen or sulphur atom or a group NH.

In one embodiment of the invention, Y represents an oxygen or sulphur atom or a group NH and $R^6$ represents —$(CH_2)_2OH$, —$(CH_2)_3OH$, hydrogen, methyl, isopropyl, methylcarbonyl or t-butylcarbonyl. In another embodiment, Y represents oxygen and $R^6$ represents hydrogen.

Preferably $R^8$, $R^9$, $R^{10}$, $R^{11}$ and $R^{12}$ each independently represent a hydrogen atom or a $C_1$-$C_4$ alkyl group.

$R^{13}$ represents hydrogen, $C_3$-$C_8$, preferably $C_3$-$C_6$, cycloalkyl, $C_3$-$C_8$, preferably $C_3$-$C_6$, cycloalkylmethyl, or $R^{13}$ represents a $C_1$-$C_6$ alkyl group optionally substituted by at least one substituent, e.g. one, two or three substituents independently selected from hydroxyl and $C_1$-$C_6$ alkoxy. Examples of preferred groups $R^{13}$ include hydrogen, —$(CH_2)_2OH$, methyl, ethyl, n-propyl, isopropyl, n-butyl, n-pentyl, n-hexyl, cyclopropyl, cyclopentyl, cyclohexyl and cyclohexylmethyl.

$R^{14}$, $R^{15}$, $R^{16}$, $R^{17}$ and $R^{18}$ each independently represent a $C_1$-$C_6$, or $C_1$-$C_4$, alkyl group.

Preferred compounds of the invention include:
2-Chloro-5-[[2-(2-hydroxy-ethylamino)-ethylamino]-methyl]-N-(tricyclo[3.3.1.1$^{3,7}$]dec-1-ylmethyl)-benzamide,
2-Chloro-5-[[2-(2-hydroxyethoxy)ethylamino]methyl]-N-(tricyclo[3.3.1.1$^{3,7}$]dec-1-ylmethyl)-benzamide,
2-Chloro-5-[(3-hydroxy-2,2-dimethylpropylamino)methyl]-N-(tricyclo[3.3.1.1$^{3,7}$]dec-1-ylmethyl)-benzamide,
2-Chloro-5-[(5-hydroxypentylamino)methyl]-N-(tricyclo[3.3.1.1$^{3,7}$]dec-1-ylmethyl)-benzamide,
2-Chloro-5-[[2-[(2-hydroxyethylthio)ethylamino]methyl]-N-(tricyclo[3.3.1.1$^{3,7}$]dec-1-ylmethyl)-benzamide,
2-Chloro-5-[3-[(2-hydroxyethyl)amino]propyl]-N-(tricyclo[3.3.1.1$^{3,7}$]dec-1-ylmethyl)-benzamide,
2-Chloro-5-[3-[(3-hydroxypropyl)amino]propyl]-N-(tricyclo[3.3.1.1$^{3,7}$]dec-1-ylmethyl)-benzamide,
2-Chloro-5-[3-(methylamino)propyl]-N-(tricyclo[3.3.1.1$^{3,7}$]dec-1-ylmethyl)-benzamide,
2-Chloro-5-[3-[(1-methylethyl)amino]propyl]-N-(tricyclo[3.3.1.1$^{3,7}$]dec-1-ylmethyl)-benzamide,
5-[3-[(2-Amino-2-methylpropyl)amino]propyl]-2-chloro-N-(tricyclo[3.3.1.1$^{3,7}$]dec-1-ylmethyl)-benzamide,
2-Chloro-5-[3-[(4-hydroxybutyl)amino]propyl]-N-(tricyclo[3.3.1.1$^{3,7}$]dec-1-ylmethyl)-benzamide,
2-Chloro-5-[3-[(2-hydroxy-2-methylpropyl)amino]propyl]-N-(tricyclo[3.3.1.1$^{3,7}$]dec-1-ylmethyl)-benzamide,
2-Chloro-5-[3-[[2-(methylamino)ethyl]amino]propyl]-N-(tricyclo[3.3.1.1$^{3,7}$]dec-1-ylmethyl)-benzamide, dihydrochloride salt,
(S)-2-Chloro-5-[3-[(2-hydroxypropyl)amino]propyl]-N-(tricyclo[3.3.1.1$^{3,7}$]dec-1-ylmethyl)-benzamide, hydrochloride salt,
(R)-2-Chloro-5-[3-[(2-hydroxypropyl)amino]propyl]-N-(tricyclo[3.3.1.1$^{3,7}$]dec-1-ylmethyl)-benzamide, hydrochloride salt,
(R)-2-Chloro-5-[3-[(2-hydroxy-1-methylethyl)amino]propyl]-N-(tricyclo[3.3.1.1$^{3,7}$]dec-1-ylmethyl)-benzamide, hydrochloride salt,
2-Chloro-5-[3-[[2-hydroxy-1-(hydroxymethyl)-1-methylethyl]amino]propyl]-N-(tricyclo[3.3.1.1$^{3,7}$]dec-1-ylmethyl)-benzamide,
5-[3-[[2-(Acetylamino)ethyl]amino]propyl]-2-chloro-N-(tricyclo[3.3.1.1$^{3,7}$]dec-1-ylmethyl)-benzamide, hydrochloride salt,
2-Chloro-5-[3-[[2-(diethylamino)ethyl]amino]propyl]-N-(tricyclo[3.3.1.1$^{3,7}$]dec-1-ylmethyl)-benzamide, dihydrochloride salt,
2-Chloro-5-[3-[(3-methoxypropyl)amino]propyl]-N-(tricyclo[3.3.1.1$^{3,7}$]dec-1-ylmethyl)-benzamide, hydrochloride salt,
2-Chloro-5-[3-[(3-hydroxy-3-methylbutyl)amino]propyl]-N-(tricyclo[3.3.1.1$^{3,7}$]dec-1-ylmethyl)-benzamide, hydrochloride salt,
2-Chloro-5-[3-[(2-methoxyethyl)amino]propyl]-N-(tricyclo[3.3.1.1$^{3,7}$]dec-1-ylmethyl)-benzamide, hydrochloride salt,
2-Chloro-5-[[3-(methylamino)propoxy]methyl]-N-(tricyclo[3.3.1.1$^{3,7}$]dec-1-ylmethyl)benzamide,
2-Chloro-5-[[2-[(2-hydroxyethyl)amino]ethoxy]methyl]-N-(tricyclo[3.3.1.1$^{3,7}$]dec-1-ylmethyl)-benzamide, acetic acid salt,
2-Chloro-5-[[2-[(3-hydroxypropyl)amino]ethoxy]methyl]-N-(tricyclo[3.3.1.1$^{3,7}$]dec-1-ylmethyl)-benzamide, acetic acid salt,
2-Chloro-5-[[[3-[(1-methylethyl)amino]propyl]amino]methyl]-N-(tricyclo[3.3.1.1$^{3,7}$]dec-1-ylmethyl)-benzamide,
5-[[(3-Aminopropyl)amino]methyl]-2-chloro-N-(tricyclo[3.3.1.1$^{3,7}$]dec-1-ylmethyl)-benzamide,
2-Chloro-5-[[[2-[(1-methylethyl)amino]ethyl]amino]methyl]-N-(tricyclo[3.3.1.1$^{3,7}$]dec-1-ylmethyl)-benzamide,
3-[[3-[4-chloro-3-[[(tricyclo[3.3.1.1$^{3,7}$]dec-1-ylmethyl)amino]-carbonyl]phenyl]propyl]amino]propanoic acid, 2,2-dimethylpropyl ester, trifluoroacetic acid salt,
5-(2-Aminoethyl)-2-chloro-N-(tricyclo[3.3.1.1$^{3,7}$]dec-1-ylmethyl)benzamide,
2-Chloro-5-[3-[(2-hydroxyethyl)pentylamino]propyl]-N-(tricyclo[3.3.1.1$^{3,7}$]dec-1-ylmethyl)-benzamide, 2-Chloro-5-[3-(methyl-2-propenylamino)propyl]-N-(tricyclo[3.3.1.1$^{3,7}$]dec-1-ylmethyl)-benzamide,
2-Chloro-5-[3-[[2-(dimethylamino)ethyl]methylamino]propyl]-N-(tricyclo[3.3.1.1$^{3,7}$]dec-1-ylmethyl)-benzamide,
5-[3-(Butylethylamino)propyl]-2-chloro-N-(tricyclo[3.3.1.1$^{3,7}$]dec-1-ylmethyl)-benzamide,
2-Chloro-5-[3-(methylpentylamino)propyl]-N-(tricyclo[3.3.1.1$^{3,7}$]dec-1-ylmethyl)-benzamide,
2-Chloro-5-[3-[[2-(diethylamino)ethyl]ethylamino]propyl]-N-(tricyclo[3.3.1.1$^{3,7}$]dec-1-ylmethyl)-benzamide,
2-Chloro-5-[3-[(2-hydroxyethyl)methylamino]propyl]-N-(tricyclo[3.3.1.1$^{3,7}$]dec-1-ylmethyl)-benzamide,
2-Chloro-5-[3-(dipropylamino)propyl]-N-(tricyclo[3.3.1.1$^{3,7}$]dec-1-ylmethyl)-benzamide,
2-Chloro-5-[3-[(2-hydroxyethyl)(1-methylethyl)amino]propyl]-N-(tricyclo[3.3.1.1$^{3,7}$]dec-1-ylmethyl)-benzamide,
5-[3-[Butyl(2-hydroxyethyl)amino]propyl]-2-chloro-N-(tricyclo[3.3.1.1$^{3,7}$]dec-1-ylmethyl)-benzamide,
2-Chloro-5-[3-(diethylamino)propyl]-N-(tricyclo[3.3.1.1$^{3,7}$]dec-1-ylmethyl)-benzamide,
2-Chloro-5-[3-(dimethylamino)propyl]-N-(tricyclo[3.3.1.1$^{3,7}$]dec-1-ylmethyl)-benzamide,
5-[3-(Butylmethylamino)propyl]-2-chloro-N-(tricyclo[3.3.1.1$^{3,7}$]dec-1-ylmethyl)-benzamide,
2-Chloro-5-[3-[(2-hydroxyethyl)propylamino]propyl]-N-(tricyclo[3.3.1.1$^{3,7}$]dec-1-ylmethyl)-benzamide,
2-Chloro-5-[3-[ethyl(2-hydroxyethyl)amino]propyl]-N-(tricyclo[3.3.1.1$^{3,7}$]dec-1-ylmethyl)-benzamide,
2-Chloro-5-[3-(dibutylamino)propyl]-N-(tricyclo[3.3.1.1$^{3,7}$]dec-1-ylmethyl)-benzamide,
2-Chloro-5-[3-(ethylpropylamino)propyl]-N-(tricyclo[3.3.1.1$^{3,7}$]dec-1-ylmethyl)-benzamide,
2-Chloro-5-[3-[methyl(1-methylethyl)amino]propyl]-N-(tricyclo[3.3.1.1$^{3,7}$]dec-1-ylmethyl)-benzamide,
2-Chloro-5-[3-[[3-(dimethylamino)propyl]methylamino]propyl]-N-(tricyclo[3.3.1.1$^{3,7}$]dec-1-ylmethyl)-benzamide,
2-Chloro-5-[3-[cyclohexyl(2-hydroxyethyl)amino]propyl]-N-(tricyclo[3.3.1.1$^{3,7}$]dec-1-ylmethyl)-benzamide,
2-Chloro-5-[3-(cyclohexylmethylamino)propyl]-N-(tricyclo[3.3.1.1$^{3,7}$]dec-1-ylmethyl)-benzamide,
2-Chloro-5-[3-(cyclohexylamino)propyl]-N-(tricyclo[3.3.1.1$^{3,7}$]dec-1-ylmethyl)-benzamide,
2-Chloro-5-[3-[[1-(hydroxymethyl)-2,2-dimethylpropyl]amino]propyl]-N-(tricyclo[3.3.1.1$^{3,7}$]dec-1-ylmethyl)-benzamide,
2-Chloro-5-[3-(cyclopropylamino)propyl]-N-(tricyclo[3.3.1.1$^{3,7}$]dec-1-ylmethyl)-benzamide,
2-Chloro-5-[3-[[2-(dimethylamino)ethyl]amino]propyl]-N-(tricyclo[3.3.1.1$^{3,7}$]dec-1-ylmethyl)-benzamide,
2-Chloro-5-[3-[(3-hydroxy-2,2-dimethylpropyl)amino]propyl]-N-(tricyclo[3.3.1.1$^{3,7}$]dec-1-ylmethyl)-benzamide,
2-Chloro-5-[3-[(1,1-dimethylethyl)amino]propyl]-N-(tricyclo[3.3.1.1$^{3,7}$]dec-1-ylmethyl)-benzamide,
2-Chloro-5-[3-[[3-(dimethylamino)propyl]amino]propyl]-N-(tricyclo[3.3.1.1$^{3,7}$]dec-1-ylmethyl)-benzamide,
2-Chloro-5-[3-(cyclopentylamino)propyl]-N-(tricyclo[3.3.1.1$^{3,7}$]dec-1-ylmethyl)-benzamide,
2-Chloro-N-(tricyclo[3.3.1.1$^{3,7}$]dec-1-ylmethyl)-5-[3-[(1,2,2-trimethylpropyl)amino]propyl]-benzamide,
5-[3-(Butylamino)propyl]-2-chloro-N-(tricyclo[3.3.1.1$^{3,7}$]dec-1-ylmethyl)-benzamide,
2-Chloro-5-[3-[[1-(hydroxyethyl)-2-methylpropyl]amino]propyl]-N-(tricyclo[3.3.1.1$^{3,7}$]dec-1-ylmethyl)-benzamide,
2-Chloro-5-[3-[(1-methylpropyl)amino]propyl]-N-(tricyclo[3.3.1.1$^{3,7}$]dec-1-ylmethyl)-benzamide,
2-Chloro-5-[3-[[2-(methylthio)ethyl]amino]propyl]-N-(tricyclo[3.3.1.1$^{3,7}$]dec-1-ylmethyl)-benzamide,
2-Chloro-5-[3-[(2-hydroxy-1,1-dimethylethyl)amino]propyl]-N-(tricyclo[3.3.1.1$^{3,7}$]dec-1-ylmethyl)-benzamide,
2-Chloro-5-[3-[(cyclohexylmethyl)amino]propyl]-N-(tricyclo[3.3.1.1$^{3,7}$]dec-1-ylmethyl)-benzamide,
2-Chloro-5-[3-(2-propenylamino)propyl]-N-(tricyclo[3.3.1.1$^{3,7}$]dec-1-ylmethyl)-benzamide,
2-Chloro-5-[3-[(2-fluoroethyl)amino]propyl]-N-(tricyclo[3.3.1.1$^{3,7}$]dec-1-ylmethyl)-benzamide,
2-Chloro-5-[3-[(2-methoxy-1-methylethyl)amino]propyl]-N-(tricyclo[3.3.1.1$^{3,7}$]dec-1-ylmethyl)-benzamide,
2-Chloro-5-[3-[3-(methylamino)propoxy]propyl]-N-(tricyclo[3.3.1.1$^{3,7}$]dec-1-ylmethyl)benzamide, dihydrochloride salt,
5-[[[(1-Aminocyclopropyl)methyl](2-hydroxyethyl)amino]methyl]-2-chloro-N-(tricyclo[3.3.1.1$^{3,7}$]dec-1-ylmethyl)-benzamide,
5-[[(2-Hydroxyethyl)[2-(methylamino)ethyl]amino]methyl]-2-methyl-N-(tricyclo[3.3.1.1$^{3,7}$]dec-1-ylmethyl)-benzamide,
2-Chloro-5-[3-[[2-(1-methyl-1H-imidazol-4-yl)ethyl]amino]propyl]-N-(tricyclo[3.3.1.1$^{3,7}$]dec-1-ylmethyl)benzamide,
2-Chloro-5-[3-[[2-(1H-imidazol-4-yl)ethyl]amino]propyl]-N-(tricyclo[3.3.1.1$^{3,7}$]dec-1-ylmethyl)benzamide,
2-Chloro-5-[3-[[3-(1H-imidazol-1-yl)propyl]amino]propyl]-N-(tricyclo[3.3.1.1$^{3,7}$]dec-1-ylmethyl)benzamide,
and pharmaceutically acceptable salts and solvates thereof.

The present invention further provides a process for the preparation of a compound of formula (I) as defined above which comprises:

(a) when X represents an oxygen or sulphur atom or a group $NR^{13}$, reaching a compound of general formula

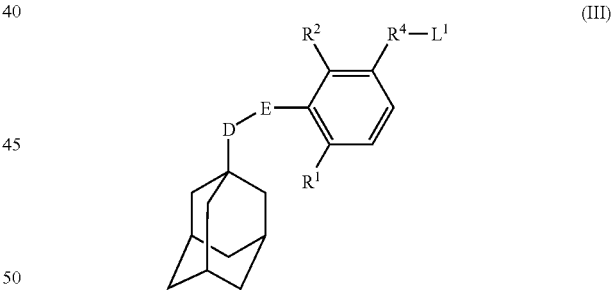

wherein $L^1$ represents a leaving group (e.g. a halogen atom or trifluoromethanesulphonate group) and D, E, $R^1$, $R^2$ and $R^4$ are as defined in formula (I), with a compound of general formula

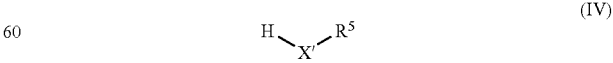

wherein X' represents an oxygen or sulphur atom or a group $NR^{13}$, and $R^5$ is as defined in formula (I), optionally in the presence of a suitable silver salt (e.g. silver trifluoromethanesulphonate); or (b) when X represents SO or $SO_2$, reacting a corresponding compound of formula (I) in which X represents a sulphur atom with a suitable oxidising agent; or (c) when X represents a group $NR^{13}$, reacting a compound of general formula

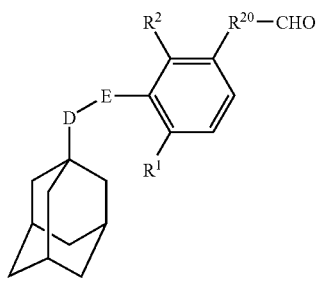

(V)

wherein $R^{20}$ represents a bond or $C_1$-$C_5$ alkyl group and D, E, $R^1$ and $R^2$ are as defined in formula (I), with a compound of general formula

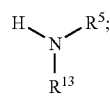

(VI)

wherein $R^5$ and $R^{13}$ are as defined in formula (I), in the presence of a reducing agent (e.g. sodium triacetoxyborohydride);

and optionally after (a), (b) or (c) converting the compound of formula (I) obtained to a pharmaceutically acceptable salt or solvate thereof.

The processes of the invention may conveniently be carried out in a solvent, e.g. an organic solvent such as dichloromethane, 1,2-dichloroethane or tetrahydrofuran, at a temperature, e.g. in the range from 0 to 200° C., preferably in the range from 0 to 150° C. The oxidising agent used in (b) above may, for example, be 3-chloroperoxybenzoic acid or potassium peroxymonosulphate, commercially sold under the trade mark "OXONE".

Compounds of formula (V) in which $R^{20}$ represents a bond may be prepared by reacting a compound of general formula

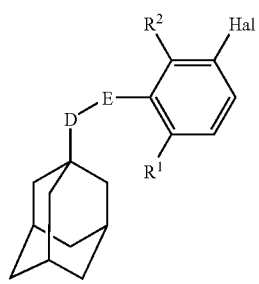

(VII)

wherein Hal represents a halogen atom such as bromine and D, E, $R^1$ and $R^2$ are as defined in formula (I), with a base such as t-butyllithium and then with a formylating agent such as dimethylformamide.

Compounds of formula (VII) may conveniently be prepared by reacting a compound of general formula

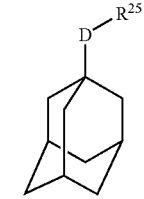

(VIII)

wherein $R^{25}$ represents $NH_2$ or $CO_2H$ and D is as defined in formula (I), with a compound of general formula

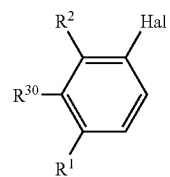

(IX)

wherein $R^{30}$ represents $CO_2H$ or $NH_2$, or $R^1$, $R^2$ and Hal are as defined in formula (VII) above.

Compounds of formula (V) in which $R^{20}$ represents a $C_1$-$C_5$ alkyl group may be prepared, for example, by reacting a corresponding compound of formula (V) in which $R^{20}$ represents a bond with (methoxymethyl)diphenylphosphineoxide in the presence of a base, or, with a compound of general formula

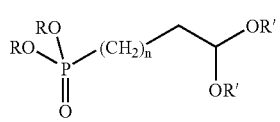

(X)

in which n is 0, 1, 2 or 3 and R and R' independently represent $C_1$-$C_6$ alkyl groups, followed by hydrogenation.

Alternatively, compounds of formula (V) in which $R^{20}$ represents a $C_2$-$C_5$ alkyl group may be prepared by reacting a compound of formula (VII) with an alkenol (e.g. 2-propen-1-ol (allyl alcohol), but-3-enol, pent-4-enol or hex-5-enol) in the presence of a palladium catalyst, optionally followed by a hydrogenation reaction and an oxidation reaction using, for example, Dess-Martin periodinane reagent (these last two steps are not required when the alkenol is allyl alcohol).

As a further alternative, compounds of formula (V) in which $R^{20}$ represents a $C_2$-$C_5$ alkyl group may be prepared by reacting a compound of formula (VII) with an alkenoate ester (e.g. methyl acrylate or ethyl acrylate) in the presence of a palladium catalyst such as palladium acetate, followed by reduction of the ester group to a hydroxyl group and then oxidation to the aldehyde with an oxidising agent (e.g. Dess-Martin periodinane reagent).

Compounds of formula (I) in which $R^5$ represents a $C_2$-$C_6$ alkyl group substituted by a group —Y—$R^6$ where Y represents O, S or NH and $R^6$ represents a group —$R^7Z$ as defined above, may be prepared by reacting a corresponding compound of formula (I) in which $R^5$ represents a $C_2$-$C_6$ alkyl group substituted by a hydroxyl group with a hydroxyl activating agent (such as methanesulphonyl chloride) in the presence of a base (such as triethylamine), followed by reaction with a compound of formula HO-R$^7$Z, HS-R$^7$Z or H$_2$N-R$^7$Z.

Compounds of formula (I) wherein E represents a group NHC(O) may be prepared from a compound of general formula

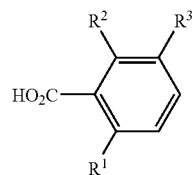
(XI)

wherein R$^1$, R$^2$ and R$^3$ are as defined in formula (I) and X represents O, S or NR$^{13}$, by reaction with adamantylmethylamine or adamantylethylamine, in the presence of a coupling agent such as 1,1'-carbonyldiimidazole.

Compounds of formula (I) wherein E represents a group C(O)NH may be prepared from a compound of general formula

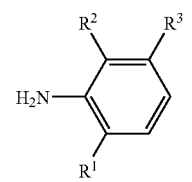
(XII)

wherein R$^1$, R$^2$ and R$^3$ are as defined in formula (I) and X represents O, S or NR$^{13}$, by reaction with adamantylacetyl chloride or adamantylpropanoyl chloride in the presence of a base such as triethylamine.

Compounds of formula (XI) can be prepared from a compound of general formula

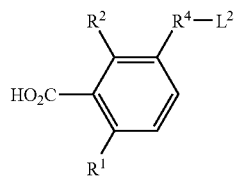
(XIII)

wherein L$^2$ represents a leaving group (such as a halogen atom or trifluoromethanesulphonate group) and R$^1$, R$^2$ and R$^4$ are as defined in formula (I), with a compound of formula (IV) as defined above, optionally in the presence of a silver salt such as silver trifluoromethanesulphonate.

Compounds of formula (XII) can be prepared from a compound of general formula

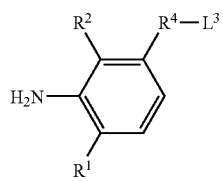
(XIV)

wherein L$^3$ represents a leaving group (such as a halogen atom or trifluoromethanesulphonate group) and R$^1$, R$^2$ and R$^4$ are as defined in formula (I), with a compound of formula (IV) as defined above, optionally in the presence of a silver salt such as silver trifluoromethanesulphonate.

It will be appreciated that certain compounds of formula (I) may be converted into further compounds of formula (I). For example, compounds of formula (I) in which —Y—R$^6$ represents —OH can be converted to compounds in which Y is O and R$^6$ is C$_1$-C$_6$ alkoxycarbonyl, by reaction with an acylating agent. Furthermore, compounds of formula (I) in which X represents NR$^{13}$ and R$^{13}$ is other than hydrogen, for example, a cyclohexyl group can be prepared by reacting a compound of formula (I) in which X represents NH with cyclohexanone in the presence of a reducing agent such as sodium triacetoxyborohydride.

Compounds of formula (III), (IV), (VI), (VIII), (IX), (X), (XIII) and (XIV) as well as compounds HO-R$^7$Z, HS-R$^7$Z and H$_2$N-R$^7$Z are either commercially available, are well known in the literature or may be prepared easily using known techniques.

It will be appreciated by those skilled in the art that in the processes of the present invention certain functional groups such as hydroxyl, carboxyl, aldehyde, carbonyl or amino groups in the starting reagents or intermediate compounds may need to be protected by protecting groups. Thus, the preparation of the compounds of formula (I) may involve at a certain stage the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compounds of the present invention are advantageous in that they possess pharmacological activity and have utility as modulators of P2X$_7$ receptor activity. They are therefore indicated as pharmaceuticals for use in the treatment or prevention of rheumatoid arthritis, osteoarthritis, psoriasis, allergic dermatitis, asthma, hyperresponsiveness of the airway, chronic obstructive pulmonary disease (COPD), bronchitis, septic shock, glomerulonephritis, irritable bowel disease, Crohn's disease, ulcerative colitis, atherosclerosis, growth and metastases of malignant cells, myoblastic leukaemia, diabetes, neurodegenerative disease, Alzheimer's disease, meningitis, osteoporosis, burn injury, ischaemic heart disease, stroke, peripheral vascular disease and varicose veins.

Accordingly, the present invention provides a compound of formula (I), or a pharmaceutically acceptable salt or solvate thereof, as hereinbelow defined for use in therapy.

In another aspect, the invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of effecting immunosuppression (e.g. in the treatment of rheumatoid arthritis, irritable bowel disease, atheroselerosis, psoriasis, pulmonary disease, e.g. COPD or bronchitis, or diseases of the central nervous system, e.g. Alzheimer's disease or stroke) which comprises administering a therapeutically effective amount of a compound of formula (I), or a pharmaceutically acceptable salt or solvate thereof, as hereinbefore defined to a patient.

For the above-mentioned therapeutic uses the dosage administered will, of course, vary with the compound employed, the mode of administration, the treatment desired and the disease or condition indicated. For effecting immunosuppression, the daily dosage of the compound of formula (I) will typically be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99%w (per cent by weight), more preferably from 0.10 to 70%w, of active ingredient, and, from 1 to 99.95%w, more preferably from 30 to 99.90%w, of a pharmaceutically acceptable adjuvant, diluent or carrier, all percentages by weight being based on total composition.

Thus, the present invention also provides a pharmaceutical composition comprising a compound of formula (I), or a pharmaceutically acceptable salt or solvate thereof, as hereinbefore defined in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The present invention will now be further explained by reference to the following illustrative examples.

EXAMPLE 1

2-Chloro-5-[[2-(2-hydroxy-ethylamino)-ethylamino]-methyl]-N-(tricyclo[3.3.1.1$^{3,7}$]dec-1-ylmethyl)-benzamide dihydrochloride

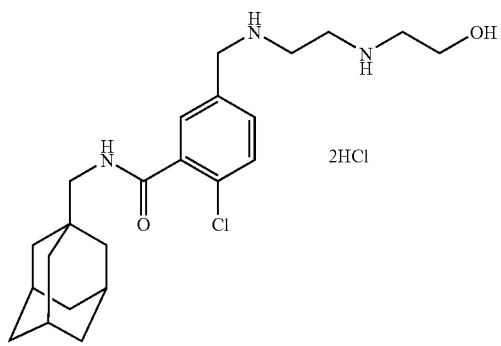

a) 5-Bromo-2-chloro-N-(tricyclo[3.3.1.1$^{3,7}$]dec-1-ylmethyl)-benzamide

To a suspension of 5-bromo-2-chlorobenzoic acid (5.00 g) in dichloromethane (25 ml) at 0° C. was added oxalyl chloride (3.7 ml) and DMF (5 drops). The resulting mixture was stirred at room temperature under a nitrogen atmosphere for 1 h, then concentrated under reduced pressure to yield a solid. The solid was dissolved in dichloromethane (20 ml) and added dropwise to a solution of 1-adamantanemethylamine (3.36 g) and N,N-diisopropylethylamine (5.55 ml) in dichloromethane (20 ml). The resulting solution was allowed to stir at room temperature under a nitrogen atmosphere for 20 hs. The reaction mixture was diluted with dichloromethane and washed with water, 10% aqueous potassium carbonate, 10% aqueous potassium hydrogen sulfate and saturated brine. The organic phase was then dried over sodium sulfate, filtered and concentrated under reduced pressure to afford the subtitled compounds as a solid (7.84 g).

MS (APCI+ve) 382/384/386 (M+H)$^+$ $^1$H NMR (DMSO-d$_6$) δ 8.42 (1H, t); 7.63 (1H, dd); 7.57 (1H, m); 7.45 (1H, d), 2.93 (2H, d); 1.94 (3H, s, br); 1.69-1.58 (6H, m); 1.51 (6H, s).

b) 2-Chloro-5-formyl-N-(tricyclo[3.3.1.1$^{3,7}$]dec-1-ylmethyl)-benzamide

A solution of 5-bromo-2-chloro-N-(tricyclo[3.3.1.1$^{3,7}$] dec-1-ylmethyl)-benzamide (3.25 g, Example 1a) in tetrahydrofuran (150 ml) was cooled to −78° C. under a nitrogen atmosphere. A solution of 1.4 M methyllithium in diethyl ether (6.1 ml) was added to this solution over 2 min. The mixture was stirred at −78° C. for 10 min., then a 1.7 M solution of tert-butyllithium in pentane (10.0 ml) was added dropwise. The mixture was stirred at −78° C. for a further 10 min., then dimethylformamide (1.0 ml) was added. The resulting solution was stirred at −78° C. for 30 min., quenched with saturated aqueous ammonium chloride solution (100 ml) and extracted with ethyl acetate. The combined extracts were dried over sodium sulfate, filtered, and the filtrate concentrated under reduced pressure to give the subtitled compound as a solid (2.76 g).

MS (APCI+ve) 332/334 (M+H)+

$^1$H NMR (DMSO-d$_6$) δ 10.04 (1H, s); 8.49 (1H, t); 7.96-7.91 (2H, m); 7.74 (1H, d); 2.96 (2H, d), 1.95 (3H, s); 1.64 (6H, m); 1.53 (6H, d).

c) 2-Chloro-5-[[2-(2-hydroxy-ethylamino)-ethylamino]-methyl]-N-(tricyclo[3.3.1.1$^{3,7}$]dec-1-ylmethyl)-benzamide dihydrochloride A mixture of 2-chloro-5-formyl-N-(tricyclo[3.3.1.1$^{3,7}$]dec-1-ylmethyl)-benzamide (0.244 g, Example 1b), 2-(2-aminoethylamino)-ethanol (0.154 g), p-toluenesulfonic acid (0.005 g) and toluene (30 ml) were refluxed together under Dean-Stark conditions for 3 hs, cooled and concentrated under reduced pressure to give an oil. This was dissolved in ethanol (30 ml) and cooled to 0° C. under a nitrogen atmosphere. Solid sodium borohydride (0.030 g) was added portionwise to this and the mixture stirred at room temperature for 30 min. The mixture was concentrated under reduced pressure and the residue purified by column chromatography over silica gel (eluting with 7:3:0.3 dichloromethane/methanol/35% aqueous ammonia) to give the free base. This was dissolved in methanol (10 ml) and treated with 4 M hydrochloric acid in dioxane (4 ml) to give a solid precipitate. This was filtered off and washed with diethyl ether to afford the title compound as a solid (0.165 g).

MS (APCI+ve) 420/422 (M+H)+

$^1$H NMR (DMSO-d$_6$) δ 8.36 (1H, t); 7.61-7.57 (3H, m); 5.31 (1H, s, br); 4.22 (2H, s, br); 3.68 (2H, s, br); 3.05 (2H, s, br); 2.95 (2H, d); 1.95 (3H, s, br); 1.69-1.59 (6H, m); 1.53 (6H, s, br).

EXAMPLE 2

2-Chloro-5-[[2-(2-hydroxyethoxy)ethylamino]methyl]-N-(tricyclo[3.3.1.1$^{3,7}$]dec-1-ylmethyl)-benzamide

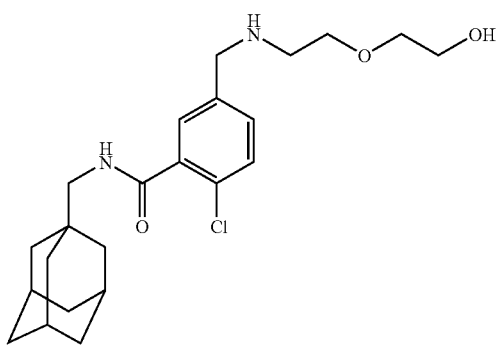

To a solution of 2-chloro-5-formyl-N-(tricyclo[3.3.1.1$^{3,7}$]dec-1-ylmethyl)-benzamide (0.150 g, Example 1b) and 2-(2-aminoethoxy)ethanol (0.065 ml) in 1,2-dichloroethane (6 ml) was added sodium triacetoxyborohydride (0.134 g), and the mixture was stirred overnight at room temperature. Water (20 ml) and dichloromethane (20 ml) were added and the layers were partitioned. The organics were washed with brine (30 ml), dried over anhydrous magnesium sulfate, filtered and concentrated under reduced pressure. The residue was purified by NPHPLC eluting with a gradient of 0-10% ethanol in dichloromethane to give the title compound as a white powder (0.016 g).

MS (APCI+ve) 421/423 (M+H)+

$^1$H NMR (DMSO-d$_6$) δ 8.29 (1H, s, br); 7.42-7.34 (3H, m); 4.60 (1H, s, br); 3.71 (2H, s); 3.47 (4H, s); 3.40 (2H, d); 2.93 (2H, d); 2.63 (2H, d); 1.94 (3H, s); 1.64 (6H, q); 1.52 (6H, s).

EXAMPLE 3

2-Chloro-5-[(3-hydroxy-2,2-dimethylpropylamino)methyl]-N-(tricyclo[3.3.1.1$^{3,7}$]dec-1-ylmethyl)-benzamide

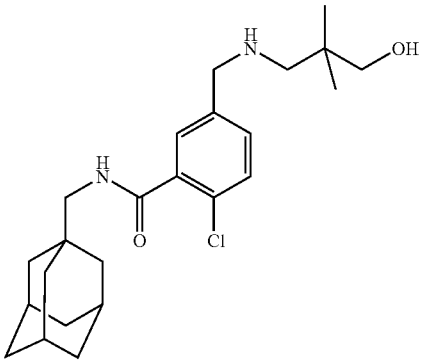

Prepared according to the method described in Example 2 from 2-chloro-5-formyl-N-(tricyclo[3.3.1.1$^{3,7}$]dec-1-ylmethyl)-benzamide (0.150 g, Example 1b), 3-amino-2,2-dimethylpropanol (0.093 g) and sodium triacetoxyborohydride (0.134 g) in 1,2-dichloroethane (6 ml). After work-up, the resiude was purified by NPHPLC eluting with a gradient of 0-10% ethanol in dichloromethane to give the title compound as a white powder (0.035 g).

MS (APCI+ve) 419/421 (M+H)+

$^1$H NMR (DMSO-d$_6$) δ 8.29 (1H, t); 7.41-7.34 (3H, m); 4.60 (1H, s, br); 3.70 (2H, s); 3.16 (2H, s); 2.93 (2H, d); 2.29 (2H, s); 1.94 (3H, s, br); 1.63 (6H, q); 1.52 (6H, d); 0.80 (6H, s).

EXAMPLE 4

2-Chloro-5-[(5-hydroxypentylamino)methyl]-N-(tricyclo[3.3.1.1$^{3,7}$]dec-1-ylmethyl)-benzamide

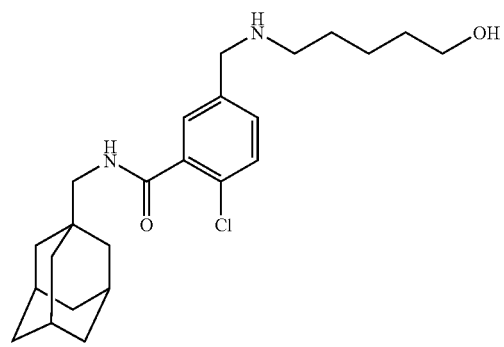

A mixture of 2-chloro-5-formyl-N-(tricyclo[3.3.1.1$^{3,7}$]dec-1-ylmethyl)-benzamide (0.100 g, Example 1b), 5-amino-1-pentanol (0.031 mg) and titanium(IV) isopropoxide (0.111 ml) was stirred under nitrogen for 1 h at room temperature. The viscous solution obtained was diluted with absolute ethanol (2 ml). Sodium cyanoborohydride (0.013 g) was added, and the solution was stirred for 20 h at room temperature. Water (5 ml) was added with stirring and the resulting precipitate was filtered and washed with ethanol. The filtrate was concentrated under reduced pressure. The crude product was dissolved in dichloromethane (20 ml) and filtered to remove the remaining inorganic residues. The filtrate was dried over anhydrous magnesium sulfate, filtered and concentrated under reduced pressure. The residue was purified by NPHPLC eluting with a gradient of 0-10% ethanol in dichloromethane to give the title compound as a white powder (0.031 g).

MS (APCI+ve) 419/421 (M)$^+$ $^1$H NMR (DMSO-d$_6$) δ 8.28 (1H, t); 7.41-7.34 (3H, m); 5.30 (1H, s); 4.31 (1H, t); 3.67 (2H, s); 3.37-3.32 (2H, m); 2.93 (2H, d); 2.46-2.42 (2H, m); 1.94 (3H, s); 1.63 (6H, q); 1.52 (6H, s); 1.43-1.36 (2H, m); 1.32-1.28 (2H, m); 1.27-1.21 (2H, m).

EXAMPLE 5

2-Chloro-5-[[2-(2-hydroxyethylthio)ethylamino]methyl]-N-(tricyclo[3.3.1.1$^{3,7}$]dec-1-ylmethyl)-benzamide

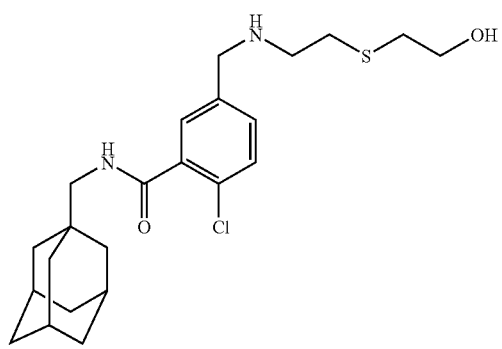

Prepared according to the method described in Example 2 from 2-chloro-5-formyl-N-(tricyclo[3.3.1.1$^{3,7}$]dec-1-ylmethyl)-benzamide (0.800 g, Example 1b), 2-(2-aminoethylthio)ethanol (0.584 g) and sodium triacetoxyborohydride (0.715 g) in 1,2-dichloroethane (15 ml). After work-up, the residue was purified by NPHPLC eluting with a gradient of 0-10% ethanol in dichloromethane to give the title compound as a white powder (0.536 g).

MS (APCI+ve) 437/439 (M)+

1H NMR (DMSO-d$_6$) δ8.29 (1H, t); 7.42-7.35 (3H, m); 4.78 (1H, s, br); 3.71 (2H, s); 3.50 (2H, t); 2.93 (2H, d); 2.68-2.58 (4H, m); 2.56-2.52 (2H, m); 1.94 (3H, s, br); 1.63 (6H, q); 1.52 (6H, s).

EXAMPLE 6

2-Chloro-5-[3-[(2-hydroxyethyl)amino]propyl]-N-(tricyclo[3.3.1.1$^{3,7}$]dec-1-ylmethyl)-benzamide, acetate salt

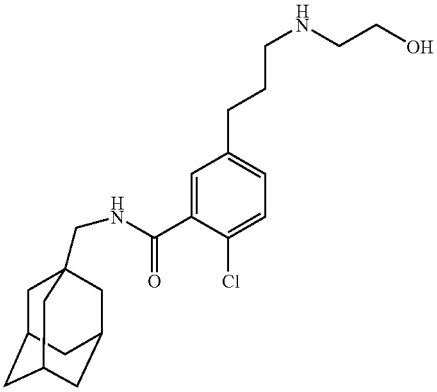

a) (2E)-3-[4-Chloro-3-[[(tricyclo[3.3.1.1$^{3,7}$]dec-1-ylmethyl)amino]carbonyl]phenyl]-2-propenoic acid, methyl ester 5-Bromo-2-chloro-N-(tricyclo[3.3.1.1$^{3,7}$]dec-1-ylmethyl)-benzamide (5 g), methyl acrylate (1.4 ml), triethylamine (2.1 ml), palladium acetate (0.070 g) and tri-orthotolyl phosphine (0.185 g) were combined in N,N-dimethylformamide (20 ml). The mixture was heated in a sealed tube under nitrogen at 90° C. for 24 h. After cooling, the reaction mixture was partitioned between dichloromethane and dilute hydrochloric acid, the mixed phases were filtered through celite and the phases separated. The organic layer was washed with dilute hydrochloric acid and brine, dried over magnesium sulfate and concentrated under reduced pressure to give a residue which was triturated with diethyl ether and filtered to yield the subtitled compound as an off white solid (4.1 g).

MS (APCI+ve) 388/390 (M+H)$^+$ $^1$H NMR (CDCl$_3$) δ 7.84 (1H, d); 7.64 (1H, d); 7.49 (1H, dd); 7.43 (1H, d); 6.45 (1H, d); 6.24 (1H, t, br); 3.81 (3H, s); 3.19 (2H, d); 2.02 (3H, s); 1.70 (6H, q); 1.59 (6H, d).

b) 4-Chloro-3-[[(tricyclo[3.3.1.1$^{3,7}$]dec-1-ylmethyl)amino]carbonyl]-benzenepropanoic acid, methyl ester 5% Rhodium on carbon (0.40 g) was added to a solution of (2E)-3-[4-chloro-3-[[(tricyclo[3.3.1.1$^{3,7}$]dec-1-ylmethyl)amino]carbonyl]phenyl]-2-propenoic acid, methyl ester (Example 6a, 2.2 g) in ethyl acetate/dichloromethane (4:1) (160 ml) and the mixture hydrogenated at 3 bar for 24 h. The catalyst was removed by filtration and the filtrate concentrated to give the subtitled compound as an oil (2.3 g).

MS (APCI+ve) 390/392 (M+H)$^+$ $^1$H NMR (CDCl$_3$) δ 7.55 (1H, d); 7.31 (1H, d); 7.20 (1H, dd); 6.26 (1H, t, br); 3.68 (3H, s); 3.17 (2H, d); 2.95 (2H, t); 2.63 (2H, t); 2.02 (3H, s); 1.70 (6H, q); 1.59 (6H, d).

c) 4-Chloro-3-[[(tricyclo[3.3.1.1$^{3,7}$]dec-1-ylmethyl)amino]carbonyl]-benzenepropanoic acid A solution of sodium hydroxide (0.475 g) in water (30 ml) was added to a solution of 4-chloro-3-[[(tricyclo[3.3.1.1$^{3,7}$]dec-1-ylmethyl-amino]carbonly]-benzenepropanoic acid, methyl ester (Example 6b, 2.3 g) in methanol (30 ml). After 5 h the reaction mixture was reduced to half volume in vacuo and acidified with dilute hydrochloric acid. A white solid precipitated and was collected by filtration and dried in vacuo at 50° C., to give the subtitled compound (1.2 g).

MS (APCI+ve) 376/378 (M+H)$^+$ $^1$H NMR (DMSO-d$_6$) δ 11.18 (1H, s); 8.28 (1H, t); 7.37 (1H, d); 7.28 (1H, dd); 7.26 (1H, d); 2.92 (2H, d); 2.82 (2H, t); 2.54 (2H, t); 1.94 (3H, s); 1.63 (6H, q); 1.52 (6H, s).

d) 2-Chloro-5-(3-hydroxypropyl)-N-(tricyclo[3.3.1.1$^{3,7}$]dec-1-ylmethyl)-benzamide Isobutylchloroformate (0.575 ml) and triethylamine (0.63 ml) were added to a solution of 4-chloro-3-[[(tricyclo[3.3.1.1$^{3,7}$]dec-1-ylmethyl)amino]carbonyl]-benzenepropanoic acid (Example 6c, 1.64 g) in tetrahydrofuran (30 ml) at 0° C. After 1 h the precipitates were removed by filtration and the filtrate added portionwise to a solution of sodium borohydride (0.18 g) in water (10 ml) at 0° C. After a further 1 h the reaction mixture was poured onto dilute hydrochloric acid and extracted with ethyl acetate. The organic phase was extracted twice with dilute hydrochloric acid, twice with saturated sodium hydrogencarbonate solution and once with brine, dried over magnesium sulfate and concentrated under reduced pressure to give a residue. Purification by silica gel chromatography (eluting with dichloromethane/methanol 96:4); yielded the subtitled compound as a solid (1.3 g).

MS (APCI+ve) 362/364 (M+H)$^+$ $^1$H NMR (CDCl$_3$) δ 7.55 (1H, d); 7.31 (1H, d); 7.19 (1H, dd); 6.28 (1H, s, br); 3.66 (2H, t); 3.17 (2H, d); 2.72 (2H, t); 1.92 (3H, s); 1.88 (2H, quin); 1.68 (6H, q); 1.59 (6H, s); 1.28 (1H, t).

e) 2-Chloro-5-[3-[(methylsulfonyl)oxy]propyl]-N-(tricyclo[3.3.1.1$^{3,7}$]dec-1-ylmethyl)-benzamide Methanesulfonyl chloride (1.1 ml) and triethylamine (2 ml) were added to a solution of 2-chloro-5-(3-hydroxypropyl)-N-(tricyclo[3.3.1.1$^{3,7}$]dec-1-ylmethyl)-benzamide (Example 6d, 2.65 g) in dichloromethane at 0° C. After 1 h the reaction mixture was diluted with ethyl acetate and extracted once with water, twice with saturated sodium hydrogencarbonate solution and once with brine, dried over magnesium sulfate and concentrated under reduced pressure to give the subtitled compound as an oil which slowly solidified (3.2 g).

MS (APCI+ve) 440/442 (M+H)$^+$ $^1$H NMR (CDCl$_3$) δ 7.55 (1H, d); 7.34 (1H, d); 7.20 (1H, dd); 6.32 (1H, t, br); 4.21 (2H, t); 3.18 (2H, d); 3.01 (3H, s); 2.77 (2H, t); 2.09 (2H, quin); 2.01 (3H, s); 1.69 (6H, q); 1.59 (6H, d).

f) 2-Chloro-5-[3-[(2-hydroxyethyl)amino]propyl]-N-(tricyclo[3.3.1.1$^{3.7}$]dec-1-ylmethyl)-benzamide, acetate salt Ethanolamine (0.07 ml) was added to a suspension of 2-chloro-5-[3-[(methylsulfonyl)oxy]propyl]-N-(tricyclo[3.3.1.1$^{3,7}$]dec-1-ylmethyl)-benzamide (Example 6e, 0.170 g) in n-butanol (5 ml) and heated at 100° C. in a sealed tube for 12 h. On cooling to ambient temperature the solution was diluted with ethyl acetate and extracted twice with saturated aqueous sodium hydrogencarbonate solution and once with brine, dried over magnesium sulfate and concentrated under reduced pressure. Purification by preperative reverse phase HPLC (eluting with a gradient of acetonitrile in 0.1% aqueous ammonium acetate/25-95%) gave the title compound as the acetate salt (0.070 g).

MS (APCI+ve) 405/407 (M+H)$^+$ $^1$H NMR (DMSO-d$_6$) δ 8.28 (1H, t); 7.36 (1H, d); 7.25 (1H, dd); 7.20 (1H, d); 3.44 (2H, t); 2.92 (2H, t); 2.50-2.65 (6H, m); 1.94 (3H, s); 1.87 (3H, s); 1.74-1.61 (8H, m); 1.52 (6H, s).

EXAMPLE 7

2-Chloro-5-[3-[(3-hydroxypropyl)amino]propyl]-N-(tricyclo[3.3.1.1$^{3,7}$]dec-1-ylmethyl)-benzamide, hydrochloride salt

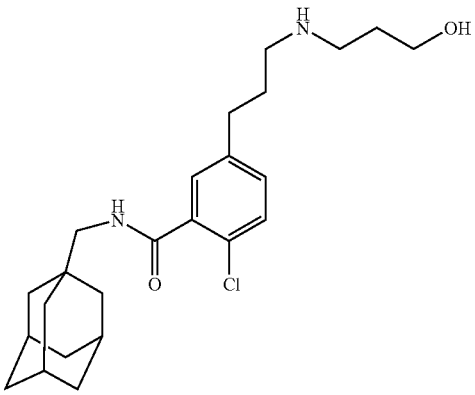

3-Aminopropanol (1ml) was added to a solution of 2-chloro-5-[3-[(methylsulfonyl)oxy]propyl]-N-(tricyclo[3.3.1.1$^{3,7}$]dec-1-ylmethyl)-benzamide (0.270 g, Example 6e) in tetrahydrofuran (30 ml) and the solution heated to reflux for 12 h. On cooling to ambient temperature the reaction mixture was diluted with water and extracted thrice with dichloromethane. The organic extracts were combined, dried over magnesium sulfate and concentrated under reduced pressure. Purification by preperative reverse phase HPLC eluting with a gradient of acetonitrile/0.1% aqueous ammonium acetate (25-95%), gave the title compound as the acetate salt. Treatment with 4 M hydrochloric acid in dioxane gave the title compound as the hydrochloride salt (0.070 g).

MS (APCI+ve) 419/421 (M+H)$^+$ $^1$H NMR (DMSO-d$_6$) δ 8.67 (2H, s); 8.31 (1H, t); 7.41 (1H, d); 7.30-7.25 (2H, m); 4.74 (1H, t); 3.47 (2H, q); 2.95-2.85 (6H, m); 2.67 (2H, t); 2.00-1.84 (5H, m); 1.76 (2H, quin); 1.63 (6H, q); 1.52 (6H, s).

EXAMPLE 8

2-Chloro-5-[3-(methylamino)propyl]-N-(tricyclo[3.3.1.1$^{3,7}$]dec-1-ylmethyl)-benzamide, acetate salt

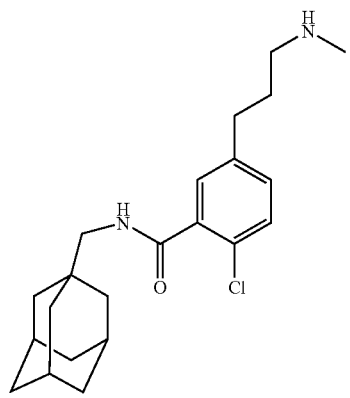

Methylamine (2 M tetrahydrofuran, 8 ml) was added to 2-chloro-5-[3-[(methylsulfonyl)oxy]propyl]-N-(tricyclo[3.3.1.1$^{3,7}$]dec-1-ylmethyl)-benzamide (0.250 g, Example 6e) and heated in a sealed tube at 70° C. for 18 h. On cooling to ambient temperature, the solution was diluted with ethyl acetate and extracted twice with saturated sodium hydrogencarbonate solution and once with brine, dried over magnesium sulfate and concentrated under reduced pressure. Purification by preperative reverse phase HPLC (eluting with a gradient of acetonitrile in 0.1% aqueous ammonium acetate/25-95%) gave the title compound as the acetate salt (0.140 g).

MS (APCI+ve) 375/377 (M+H)+

$^1$H NMR (DMSO-d$_6$) δ 8.30 (1H, t); 7.37 (1H, d); 7.24 (1H, dd); 7.21 (1H, d); 2.92 (2H, d); 2.62 (2H, t); 2.53 (2H, t); 2.30 (3H, s); 1.94 (3H, s); 1.86 (3H, s); 1.57-1.77 (8H, m); 1.52 (6H, s).

EXAMPLE 9

2-Chloro-5-[3-[(1-methylethyl)amino]propyl]-N-(tricyclo[3.3.1.1$^{3,7}$]dec-1-ylmethyl)-benzamide, hydrochloride salt

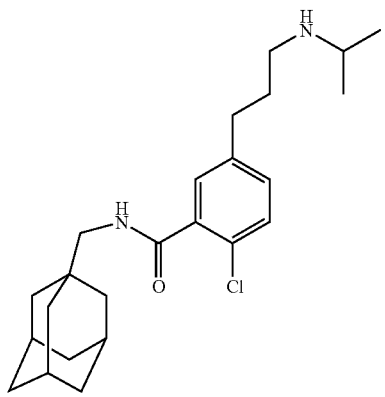

Isopropylamine (0.5 ml) was added to a solution of 2-chloro-5-[3-[(methylsulfonyl)oxy]propyl]-N-(tricyclo [3.3.1.1$^{3,7}$]dec-1-ylmethyl)-benzamide (0.250 g, Example 6e) in tetrahydrofuran (20 ml) and heated at 70° C. in a sealed tube for 24 h. The mixture was concentrated under reduced pressure and the residue purified by solid phase extraction on SCX resin. The title produce was isolated as the hydrochloric acid salt (0.10 g).

MS (APCI+ve) 403/405 (M+H)+

$^1$H NMR (DMSO-d$_6$) δ 8.67 (2H, s); 8.31 (1H, t); 7.41 (1H, d); 7.30 (1H, dd); 7.26 (1H, d); 3.33-3.22 (1H, m); 2.93 (2H, d); 2.87 (2H, s); 2.69 (2H, t); 1.86-1.95 (5H, m); 1.63 (6H, q); 1.52 (6H, s); 1.22 (6H, d).

EXAMPLE 10

5-[3-[(2-Amino-2-methylpropyl)amino]propyl]-2-chloro-N-(tricyclo[3.3.1.1$^{3,7}$]dec-1-ylmethyl)-benzamide, dihydrochloride salt

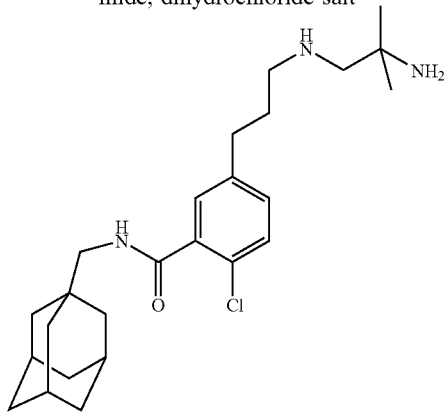

2-Methyl-1,2-propanediamine (0.12 ml) was added to a solution of 2-chloro-5-[3-[(methylsulfonyl)oxy]propyl]-N-(tricyclo[3.3.1.1$^{3,7}$]dec-1-ylmethyl)-benzamide (0.250 g, Example 6e) in tetrahydrofuran (4 ml) and heated at 60° C. in a sealed tube for 12 h. On cooling to ambient temperature, the mixture was diluted with ethyl acetate and extracted twice with saturated sodium hydrogencarbonate solution and once with brine, dried over magnesium suflate and concentrated under reduced pressure. Purification by preperative reverse phase HPLC (eluting with a gradient of acetonitrile in 0.1% aqueous ammonium acetate/25-95%) gave the title compound as the acetate salt. Treatment with 4 M hydrochloric acid in dioxane gave the title compound as the dihydrochloride salt (0.045 g).

MS (APCI+ve) 432/434 (M+H)+

$^1$H NMR (DMSO-d$_6$) δ 9.40 (2H, m); 8.60 (3H, m); 8.32 (1H, t); 7.41 (1H, d); 7.31 (1H, d); 7.27 (1H, s); 3.20 (2H, s); 2.92 (4H, d); 2.71 (2H, t); 2.01 (2H, quin); 1.94 (3H, s); 1.63 (6H, q); 1.52 (6H, s); 1.39 (6H, s).

EXAMPLE 11

2-Chloro-5-[3-[(4-hydroxybutyl)amino]propyl]-N-(tricyclo[3.3.1.1$^{3,7}$]dec-1-ylmethyl)-benzamide

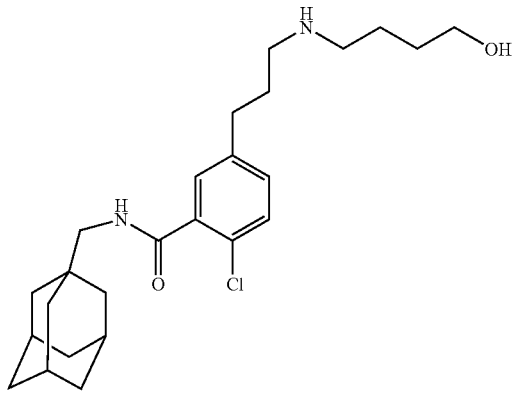

4-Amino-1-butanol (0.11 ml) was added to a solution of 2-chloro-5-[3-[(methylsulfonyl)oxy]propyl]-N-(tricyclo [3.3.1.1$^{3,7}$]dec-1-ylmethyl)-benzamide (0.25 g, Example 6e) in tetrahydrofuran (4 ml) and heated at 60° C. in a sealed tube for 12 h. On cooling to ambient temperature, the mixture was diluted with ethyl acetate and extracted twice with saturated aqueous sodium hydrogencarbonate solution and once with brine, dried over magnesium sulfate and concentrated under reduced pressure. Purification by preperative reverse phase HPLC (eluting with a gradient of acetonitrile in 0.1% aqueous ammonium acetate/25-95%) gave the title compound as the acetate salt. Treatment with aqueous 2 M sodium hydroxide and extraction into ethyl acetate gave the title compound (0.065 g).

MS (APCI+ve) 433/435 (M+H)+

$^1$H NMR (DMSO-d$_6$) δ 8.28 (1H, t); 7.35 (1H, d); 7.24 (1H, dd); 7.20 (1H, d); 3.37 (2H, t); 2.92 (2H, d); 2.63 (2H, t); 2.40-2.60 (4H, m); 1.92 (3H, s); 1.70-1.55 (8H, m); 1.52 (6H, s); 1.40-1.45 (4H, m).

EXAMPLE 12

2-Chloro-5-[3-[(2-hydroxy-2-methylpropyl)amino]propyl]-N-(tricyclo[3.3.1.1³,⁷]dec-1-ylmethyl)-benzamide, acetate salt

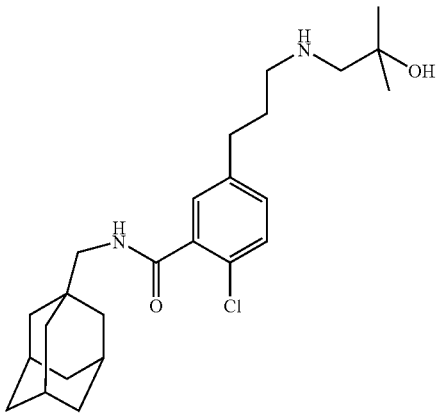

2-Hyrdroxy-2-methyl-1-propylamine [prepared according to Journal American Chemical Society (1941), 63, p1034] (0.25 ml) was added to a solution of 2-chloro-5-[3-[(methylsulfonyl)oxy]proply]-N-(tricyclo[3.3.1.1³,⁷]dec-1-ylmethyl)-benzamide (0.25 g, Example 6e) in butan-1-ol (8 ml) and heated at 100° C. in a sealed tube for 24 h. On cooling to ambient temperature, the mixture was diluted with ethyl acetate and extracted twice with saturated aqueous sodium hydrogencarbonate solution and once with brine, dried over magnesium sulfate and concentrated under reduced pressure. The residue was purified by solid phase extraction on SCX resin and preperative reverse phase HPLC (eluting with a gradient of acetonitrile in 0.1% aqueous ammonium acetate/25-95%) to give the title compound as the acetate salt (0.160 g).

MS (APCI+ve) 433/435 (M+H)⁺

¹H NMR (DMSO-d₆) δ 8.29 (1H, t); 7.36 (1H, d); 7.26 (1H, d); 7.21 (1H, s); 2.92 (2H, d); 2.63 (2H, t); 2.55 (2H, t); 2.40 (2H, s); 1.94 (3H, s); 1.88 (3H, s); 1.80-1.58 (8H, m); 1.52 (6H, s); 1.08 (6H, s).

EXAMPLE 13

2-Chloro-5-[3-[[2-(methylamino(ethyl]amino]propyl]-N-(tricyclo[3.3.1.1³,⁷]dec-1-ylmethyl)-benzamide, dihydrochloride salt

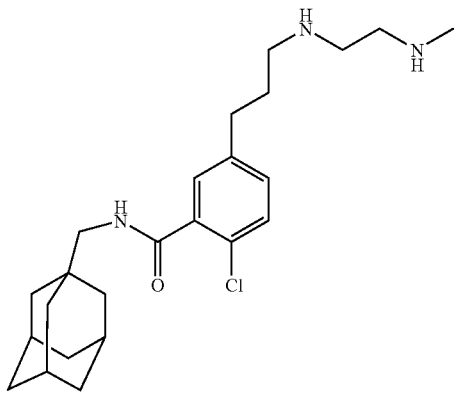

a) 2-Chloro-5-(3-oxopropyl)-benzoic acid

2-Chloro-5-iodobenzoic acid (5.0 g), tetrabutylammonium chloride (5.0 g), sodium hydrogencarbonate (5.3 g) and allyl alcohol (1.6 ml) were combined in N,N-dimethylformamide (50 ml) and PdCl₂ (0.6 g) was added under nitrogen. After 24 h ethyl acetate and 2 M hydrochloric acid were added to the crude reaction mixture and the precipitated Pd filtered off. The organic phase was separated and washed thrice with 2 M hydrochloric acid then once with brine and dried over magnesium sulfate, filtered and evaporate. Purification by chromatography on silica (eluting ethyl acetate:acetic acid/19:1) gave the subtitled product as an oil (2.77 g).

MS m/z 212/214

¹H NMR (CDCl₃) δ 9.82 (1H, s); 7.83 (1H, d); 7.42 (1H, d); 7.30 (1H, dd); 2.98 (2H, t); 2.83 (2H, t).

b) 2-Chloro-5-[3-[[(1,1-dimethylethoxy)carbonyl][2-[[(1,1-dimethylethoxy)carbonyl]methylamino]ethyl]amino]propyl]-benzoic acid Sodium triacetoxyborohydride (310 mg) was added to a solution of (2-aminoethyl)methyl-1,1-dimethylethyl carbamic acid ester [prepared according to J.Med.Chem (1990), 33(1), 100] (0.156 g) and 2-chloro-5-(3-oxopropyl)-benzoic acid (0.21 g, Example 13a) in methanol (15 ml). After 24 h, acetic acid (0.2 ml) was added and the mixture evaporated to dryness. The residue was redissolved in dichloromethane (10 ml), triethylamine (0.45 ml) and (1,1-dimethylethoxy)carbonyl 1,1-dimethylethyl carbonic acid ester (1 g) was added. After 24 h the reaction mixture was washed twice with 10% KHSO₄, once with brine and dried over magnesium sulfate, filtered and evaporated. Purification by chromatography on silica (eluting with iso-hexane:ethy acetate: acetic acid/80:20:1 then ethyl acetate:acetic acid/100:1) gave the subtitled product as an oil (0.2 g).

MS (APCI+ve) 471/473 (M+H)⁺ c) 2-Chloro-5-[3-[[2-(methylamino)ethyl]amino]propyl]-N-(tricyclo[3.3.1.1³,⁷]dec-1-ylmethyl)-benzamide, dihydrochloride salt PyBrOP (0.2 g) was added to a solution of 2-chloro-5-[3-[[(1,1-dimethylethoxy)carbonyl][2-[[(1,1-dimethylethoxy)carbonyl]methylamino]ethyl]-amino]propyl]-benzoic acid (0.2 g, Example 13b), adamantanemethylamine (0.1 ml) and triethylamine (0.15 ml) in N,N-dimethylformamide (10 ml). After 1 h the reaction mixture was diluted with ethyl acetate and washed with water, then washed twice with ammonium chloride solution, twice with saturated sodium hydrogencarbonate solution and once with brine. The organic extracts were dried over magnesium sulfate, filtered, evaporated and purified by chromatography on silica (eluting with dichloromethane:methanol/2-10%). The product was redissolved in dichloromethane:methanol/1:1 (15 ml) and 4 M hydrochloric acid in dioxane (2 ml) added. The mixture was stirred until deprotection was complete then purified by prep RP-HPLC (acetonitrile/0.1% aqueous trifluoroacetic acid). Conversion to the hydrochloride salt by treatment with 4 M hydrochloric acid in 1,4-dioxane/methanol gave the title compound (0.055 g).

MS (APCI+ve) 418/420 (M+H)⁺

¹H NMR (DMSO-d₆) δ 9.50-9.00 (4H, m); 7.42 (1H, d); 7.29 (1H, d); 7.27 (1H, s); 3.25 (4H, s, br); 3.05-2.90 (4H, m); 2.70 (2H, t); 2.60 (3H, s); 2.00-1.90 (5H, m); 1.63 (6H, q); 1.52 (6H, s).

EXAMPLE 14

(S)-2-Chloro-5-[3-[(2-hydroxyproply)amino]propyl]-N-(tricyclo[3.3.1.1$^{3,7}$]dec-1-ylmethyl)-benzamide, hydrochloride salt

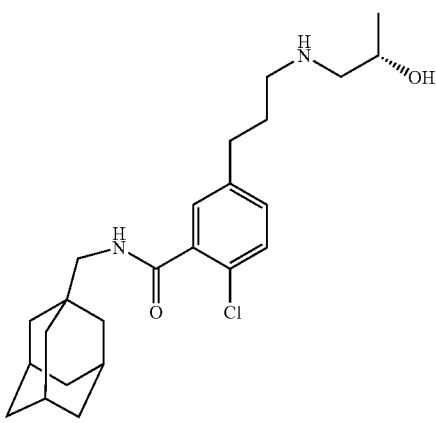

a) 2-Chloro-5-iodo-N-(tricyclo[3.3.1.1$^{3,7}$]dec-1-ylmethyl)-benzamide

2-Chloro-5-iodobenzoic acid (10.0 g) was suspended in dichloromethane (160 ml) then oxalyl chloride (4.0 ml) was added followed by N,N-dimethylformamide (40 μl). After 24 h the solvent was evaporated to afford a white solid, which was redissolved in dichloromethane (160 ml). Triethylamine (14.8 ml) was added followed by adamantylmethylamine (6.9 ml) with cooling to maintain a temperature below 30° C. The resulting cloudy mixture was stirred for 1 h, then evaporated to give a pale yellow solid. This was stirred in a mixture of ethyl acetate (400 ml) and 2 M hydrochloric acid (300 ml) until the solid dissolved to give 2 clear phases. The (upper) organic phase was separated and washed with 2 M aqueous sodium hydroxide solution (300 ml), then dried (Na₂SO₄) and evaporated to a yellow solid. The solid was suspended in iso-hexane (100 ml), then filtered and washed with more iso-hexane (40 ml). The resulting off-white solid was dried in a vacuum oven at 40° C. (14.0 g).

MS (APCI+ve) 430/432 (M+H)⁺

¹H NMR (CDCl₃) δ 8.00 (1H, d); 7.66 (1H, dd); 7.14 (1H, d); 6.17 (1H, s, br); 3.17 (2H, d); 2.01 (3H, s); 1.69 (6H, q); 1.58 (6H, d).

b) 2-Chloro-5-(3-oxopropyl)-N-(tricyclo[3.3.1.1$^{3,7}$]dec-1-ylmethyl)-benzamide 2-Chloro-5-iodo-N-(tricyclo[3.3.1.1$^{3,7}$]dec-1-ylmethyl)-benzamide (5.00 g, Example 14a), tetrabutylammonium chloride (3.40 g) and sodium hydrogencarbonate (2.44 g) were charged to a flask. Pd(OAc)₂ (0.0533 g), toluene (50 ml) and allyl alcohol (1.01 ml) were added to afford a pale brown mixture which was heated at 80° C. for 5 h. The resulting dark brown mixture was cooled to ambient then filtered to remove the solid residues. These were washed with further toluene (2×50 ml) and the combined toluene extracts then washed with water (100 ml), dried over MgSO₄ and concentrated to a light brown solid (3.82 g).

MS (APCI+ve) 360/362 (M+H)⁺

¹H NMR (CDCl₃) δ 9.81 (1H, s), 7.56 (1H, s); 7.32 (1H, d); 7.19 (1H, d); 6.28 (1H, s, br); 3.18 (2H, d); 2.96 (2H, t); 2.81 (2H, t); 2.01 (3H, s); 1.70 (6H, q); 1.58 (6H, s).

c) (S)-2-Chloro-5-[3-[(2-hydroxyproply)amino]propyl]-N-(tricyclo[3.3.1.1$^{3,7}$]dec-1-ylmethyl)-benzamide, hydrochloride salt Sodium triacetoxyborohydride (0.6 g) was added to a solution of 2-chloro-5-(3-oxopropyl)-N-(tricyclo[3.3.1.1$^{3,7}$]dec-1-ylmethyl)-benzamide (0.5 g, Example 14b) and (S)-2-hyroxypropylamine (0.31 g) in dichloromethane (5 ml). After 24 h the crude reaction mixture was purified by flash chromatography (eluting with 5-20% methanol in dichloromethane+1% ammonia) and the hydrochloride salt precipitated from ether/methanol 19:1, to afford the title compound as a white solid (0.19 g).

MS (APCI+ve) 419/421 (M+H)⁺

¹H NMR (DMSO-d₆) δ 8.70-8.40 (2H, d, br); 8.30 (1H, t); 7.41 (1H, d); 7.28 (1H, dd); 7.24 (1H, d); 5.32 (1H, d); 3.97-3.90 (1H, m); 3.00-2.85 (5H, m); 2.75 (1H, t); 2.65 (2H, t); 2.00-1.90 (5H, m); 1.64 (6H, q); 1.52 (6H, s); 1.09 (3H, d).

EXAMPLE 15

(R)-2-Chloro-5-[3-[(2-hydroxyproply)amino]propyl]-N-(tricyclo[3.3.1.1$^{3,7}$]dec-1-ylmethyl)-benzamide, hydrochloride salt

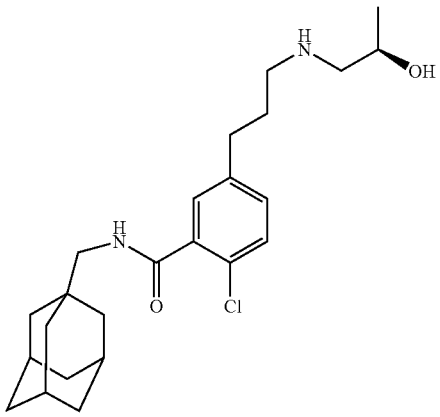

Prepared according to the method described for Example 14.

MS (APCI+ve) 419/421 (M+H)⁺

¹H NMR (DMSO-d₆) δ 8.70-8.40 (2H, d, br); 8.30 (1H, t); 7.41 (1H, d); 7.28 (1H, dd); 7.24 (1H, d); 5.32 (1H, d); 3.97-3.90 (1H, m); 3.00-2.85 (5H, m); 2.75 (1H, t); 2.65 (1H, t); 2.00-1.90 (5H, m); 1.64 (6H, q); 1.52 (6H, s); 1.09 (3H, d).

EXAMPLE 16

(R)-2-Chloro-5-[3-[(2-hydroxy-1-methylethyl)amino]propyl]-N-(tricyclo[3.3.1.1$^{3,7}$]dec-1-ylmethyl)-benzamide, hydrochloride salt

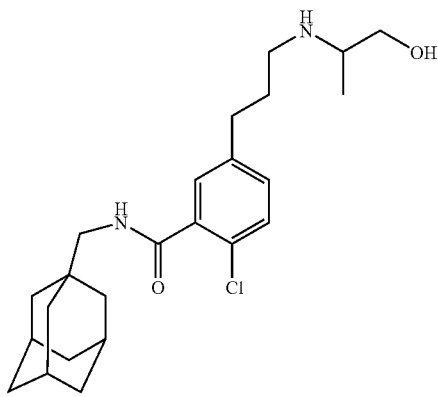

Prepared according to the method described for Example 14.

MS (APCI+ve) 419/421 (M+H)$^+$ $^1$H NMR (DMSO-$_6$) δ 8.80-8.40 (2H, d, br); 8.31 (1H, t); 7.42 (1H, d); 7.28 (1H, dd); 7.25 (1H, d); 5.36 (1H, s); 3.65-3.60 (1H, d, br); 3.55-3.45 (1H, m); 3.25-3.15 (1H, m); 2.95-2.85 (4H, m); 2.65 (2H, t); 2.00-1.90 (5H, m); 1.63 (6H, q); 1.52 (6H, s); 1.20 (3H, d).

EXAMPLE 17

2-Chloro-5-[3-[[2-hydroxy-1-(hydroxymethyl)-1-methylethyl]amino]propyl]-N-(tricyclo[3.3.1.1$^{3,7}$]dec-1-ylmethyl)-benzamide

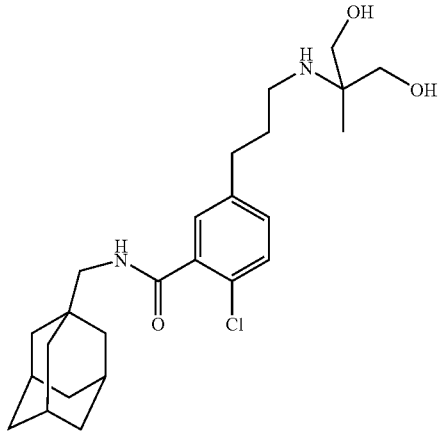

Prepared according to the method described for Example 14.

MS (APCI+ve) 449/451 (M+H)$^+$ $^1$H NMR (DMSO-d$_6$) δ 8.27 (1H, t); 7.36 (1H, d); 7.24 (1H, dd); 7.21 (1H, d); 4.32 (2H, s); 3.22 (4H, s); 2.92 (2H, d); 2.65 (2H, t); 2.45 (2H, q(on edge of DMSO)); 1.92 (3H, s); 1.70-1.57 (8H, m); 1.52 (6H, s); 0.85 (3H, s).

EXAMPLE 18

5-[3-[[2-(Acetylamino)ethyl]amino]propyl]-2-chloro-N-(tricyclo[3.3.1.1$^{3,7}$]dec-1-ylmethyl)-benzamide, hydrochloride salt

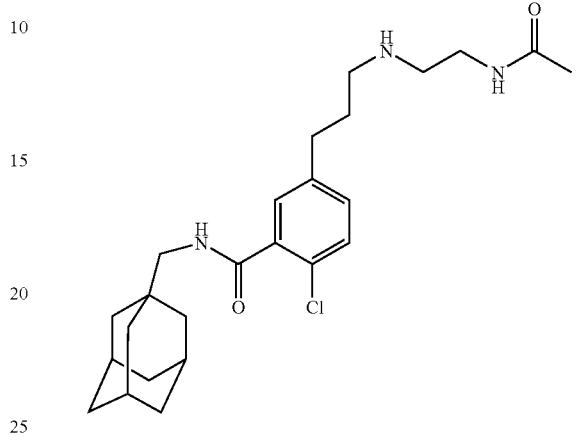

Prepared according to the method described for Example 14.

MS (APCI+ve) 446/448 (M+H)$^+$ $^1$H NMR (DMSO-d$_6$) δ 8.90 (2H, s, br); 8.32 (1H, t); 8.22 (1H, t); 7.41 (1H, d); 7.28 (1H, dd); 7.24 (1H, d); 3.33 (2H, q); 2.95-2.85 (6H, m); 2.63 (2H, t); 2.00-1.86 (5H, m); 1.84 (3H, s); 1.63 (6H, q); 1.52 (6H, s).

EXAMPLE 19

2-Chloro-5-[3-[[2-(diethylamino)ethyl]amino]propyl]-N-(tricyclo[3.3.1.1$^{3,7}$]dec-1-ylmethyl)-benzamide, dihydrochloride salt

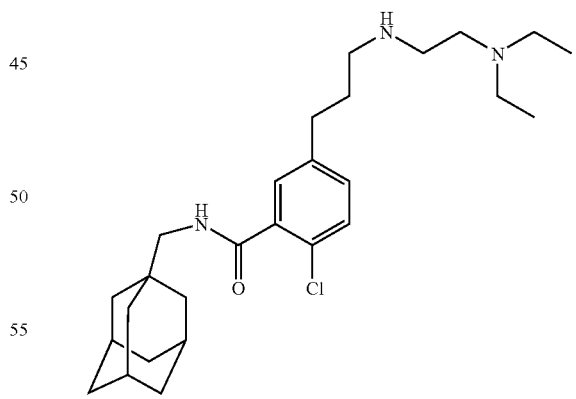

Prepared according to the method described for Example 14.

MS (APCI+ve) 460/462 (M+H)$^+$ $^1$H NMR (DMSO-d$_6$) δ 10.70 (1H, s); 9.48 (2H, s); 8.31 (1H, t); 7.42 (1H, d); 7.30 (1H, dd); 7.27 (1H, d); 3.50-3.30 (2H, m); 3.25-3.10 (4H, m); 3.00-2.90 (4H, d, br); 2.71 (2H, t); 2.00-1.90 (5H, m); 1.63 (6H, q); 1.52 (6H, s); 1.24 (6H, t).

EXAMPLE 20

2-Chloro-5-[3-[(3-methoxypropyl)amino]propyl]-N-(tricyclo[3.3.1.1$^{3,7}$]dec-1-ylmethyl)-benzamide, hydrochloride salt

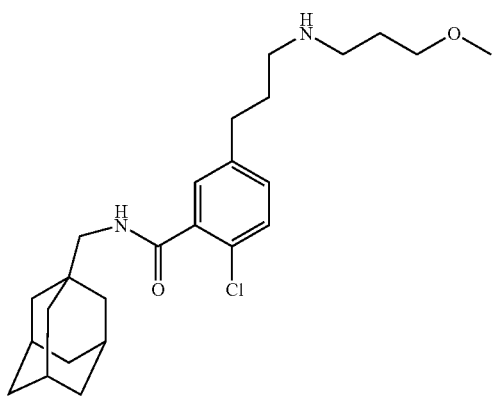

Prepared according to the method described for Example 14.

MS (APCI+ve) 433/435 (M+H)$^+$ $^1$H NMR (DMSO-d$_6$) δ 8.77 (2H, s, br); 8.31 (1H, t); 7.41 (1H, d); 7.28 (1H, dd); 7.25 (1H, d); 3.40 (2H, t); 3.23 (3H, s); 3.00-2.75 (6H, m); 2.67 (2H, t); 2.00-1.80 (7H, m); 1.63 (6H, q); 1.52 (6H, s).

EXAMPLE 21

2-Chloro-5-[3-[(3-hydroxy-3-methylbutyl)amino]propyl]-N-(tricyclo[3.3.1.1$^{3,7}$]dec-1-ylmethyl)-benzamide, hydrochloride salt

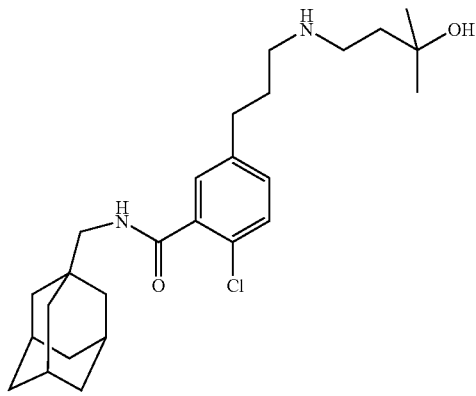

Prepared according to the method described for Example 14.

MS (APCI+ve) (M+H)$^+$ $^1$H NMR (DMSO-d$_6$) δ 8.57 (2H, s, br); 8.30 (1H, t); 7.42 (1H, d); 7.29 (1H, dd); 7.25 (1H, d); 4.61 (1H, s); 3.05-2.85 (6H, m); 2.64 (2H, t); 2.00-1.82 (5H, m); 1.73-1.53 (8H, m); 1.52 (6H, s); 1.12 (6H, s).

EXAMPLE 22

2-Chloro-5-[3-[(2-methoxyethyl)amino]propyl]-N-(tricyclo[3.3.1.1$^{3,7}$]dec-1-ylmethyl)-benzamide, hydrochloride salt

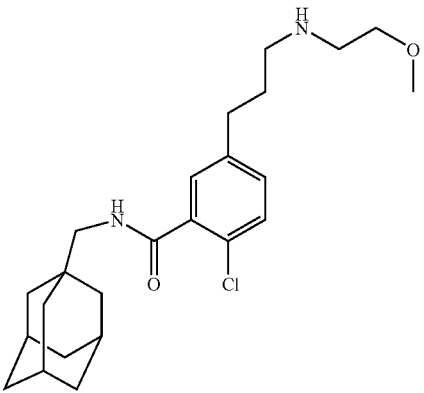

Prepared according to the method described for Example 14.

mp 245-248° C.

MS (APCI+ve) 419/421 (M+H)$^+$ $^1$H NMR (DMSO-d$_6$) δ 8.79 (2H, s); 8.30 (1H, t); 7.41 (1H, d); 7.27 (1H, dd); 7.25 (1H, d); 3.58 (2H, t); 3.30 (3H, s); 3.09 (2H, s, br); 2.95-2.85 (4H, m); 2.67 (2H, t); 1.95-1.86 (5H, m); 1.63 (6H, q); 1.52 (6H, s).

EXAMPLE 23

2-Chloro-5-[[3-(methylamino)propoxy]methyl]-N-(tricyclo[3.3.1.1$^{3,7}$]dec-1-ylmethyl)benzamide

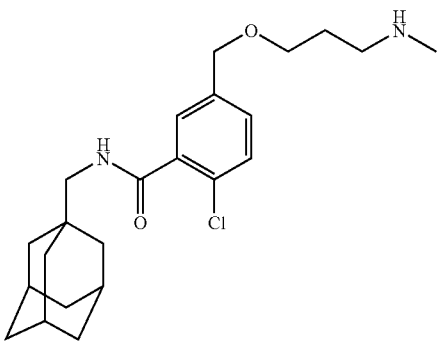

a) 2-Chloro-5-[[3-[[(1,1-dimethylethoxy)carbonyl]methylamino]propoxy]methyl]-benzoic acid (3-Hydroxypropyl)methyl-carbamic acid, 1,1-dimethylethyl ester (0.272 g) in tetrahydrofuran (5 ml) was cooled to 0° C. under nitrogen. Sodium hydride (60% dispersion in oil, 0.110 g) was added. The mixture was allowed to warm to room temperature and stirred for 30 min. 5-(Bromomethyl)-2-chloro-benzoic acid (0.300 g) in tetrahydrofuran (3 ml) was added and the mixture heated at 55° C. for 6 h. The solution was cooled, poured into saturated aqueous potassium hydrogensulfate solution, extracted into ethyl acetate (×3), dried over magnesium sulfate, filtered and concentrated under reduced pressure to afford the subtitled compound (0.431 g).

MS (ESI+ve) 358 (M+H)$^+$ (ESI−ve) 356 (M−H)$^+$ b) [3-[[4-Chloro-3-[[(tricyclo[3.3.1.1$^{3,7}$]dec-1-ylmethyl)amino]carbonyl]phenyl]-methoxy]propyl]methyl-carbamic acid, 1,1-dimethylethyl ester 2-Chloro-5-[[3-[[(1,1-dimethylethoxy)carbonyl]methylamino]propoxy]methyl]-benzoic acid (0.318 g, Example 23a), carbonyl diimidazole (0.165 g) and dimethylformamide (10 ml) were heated at 50° C. under nitrogen for 30 min. The mixture was allowed to cool to room temperature and 1-adamantanemethylamine (0.18 ml) was added. The mixture was stirred at room temperature for 20 h then poured into ethyl acetate and washed with saturated aqueous sodium hydrogencarbonate solution followed by brine. The solution was dried over magnesium sulfate, filtered and concentrated under reduced pressure. The residue was purified by column chromatography over silica gel (eluting with 2:1 isohexane/ethyl acetate) to afford the subtitled compound (0.236 g).

MS (ESI+ve) 505 (M+H)$^+$ c) 2-Chloro-5-[[3-(methylamino)propoxy]methyl]-N-(tricyclo[3.3.1.1$^{3,7}$]dec-1-ylmethyl)-benzamide

[3-[[4-Chloro-3-[[(tricyclo[3.3.1.1$^{3,7}$]dec-1-ylmethyl)amino]carbonyl]phenyl]-methoxy]propyl]methyl-carbamic acid, 1,1-dimethylethyl ester (0.236 g, Example 23b), 4 M hydrogen chloride in 1,4-dioxane (5 ml) and methanol (5 ml) were stirred together under nitrogen for 3 h, then poured into 25% aqueous ammonia solution and concentrated under reduced pressure to give the free base. This was purified by column chromatography over silica gel, eluting with 19:1:0.1/dichloromethane:methanol:ammonia to afford the title compound as an oil (0.106 g).

MS (APCI+ve) 405/407 (M+H)$^+$ $^1$H NMR (CDCl$_3$) δ 7.64 (1H, s); 7.39-7.33 (2H, m); 6.29 (1H, t, br); 4.49 (2H, s); 3.55 (2H, t); 3.18-3.17 (2H, d); 2.72-2.68 (2H, t); 2.44 (3H, s); 2.01 (3H, s, br); 1.86-1.79 (2H, m); 1.75-1.63 (6H, m); 1.59 (6H, s).

EXAMPLE 24

2-Chloro-5-[[2-[(2-hydroxyethyl)amino]ethoxy]methyl]-N-(tricyclo[3.3.1.1$^{3,7}$]dec-1-ylmethyl)-benzamide, acetic acid salt

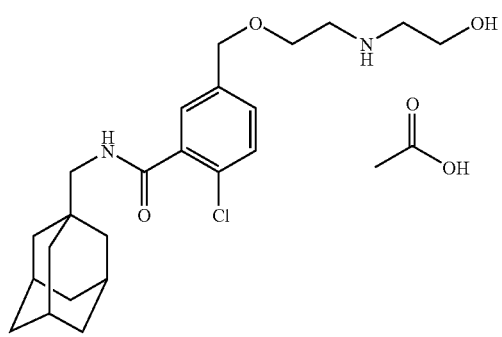

a) 5-(Bromomethyl)-2-chloro-N-(2-tricyclo[3.3.1.1$^{3,7}$]dec-1-ylmethyl)-benzamide To a solution of 2-chloro-5-(bromomethyl)-benzoic acid (1.0 g) in dichloromethane (25 ml) at 0° C. was added dimethylformamide (0.05 ml) followed by oxalyl chloride (0.52 ml). The reaction was allowed to warm to room temperature and stirred for 30 min. The volatiles were removed under vacuum and the residue dried under high vacuum. The residue was dissolved in dichloromethane (20 ml) and added to a solution of 2-adamantanemethylamine hydrochloride salt (0.95 g) in dichloromethane (20 ml) and diisopropylethylamine (2 ml) at 0° C. The reaction was allowed to warm to room temperature and stirred for 2 h. The organics were washed with water (20 ml) then saturated aqueous ammonium chloride solution and the organic layer dried over magnesium sulfate then filtered. The filtrate was concentrated under reduced pressure to a solid. The crude material was recrystallised from dichloromethane/hexane to afford the subtitled compound as a white solid (1.3 g).

b) [2-[[4-Chloro-3-[[(tricyclo[3.3.1.1$^{3,7}$]dec-1-ylmethyl)amino]carbonyl]phenyl]-methoxy]ethyl](2-hydroxyethyl)-carbamic acid, 1,1-dimethylethyl ester A mixture of 5-(bromomethyl)-2-chloro-N-(2-tricyclo[3.3.1.1$^{3,7}$]dec-1-ylmethyl)-benzamide (Example 24a, 0.300 g), bis(2-hydroxyethyl)-carbamic acid, 1,1-dimethylethyl ester (0.312 g) and silver trifluoroacetate (0.336 g) in dichloromethane (30 ml) was stirred under nitrogen at room temperature for 20 h. The solution was then decanted from the silver salts and the dichloromethane removed under vacuum. The crude material was purified on silica gel (eluting with ethyl acetate) to afford the subtitled compound as an oil (0.249 g).

MS (ESI+ve) MW 521/523 (M+H)$^+$ c) 2-Chloro-5-[[2-[(2-hydroxyethyl)amino]ethoxy]methyl]-N-(tricyclo[3.3.1.1$^{3,7}$]dec-1-ylmethyl)-benzamide, acetic acid salt

[2-[[4-Chloro-3-[[(tricyclo[3.3.1.1$^{3,7}$]dec-1-ylmethyl)amino]carbonyl]phenyl]-methoxy]ethyl](2-hydroxyethyl)-carbamic acid, 1,1-dimethylethyl ester (0.286 g, Example 23b), 4 M hydrogen chloride in 1,4-dioxane (10 ml) and methanol (10 ml) were stirred together under nitrogen for 20 h, poured into 25% aqueous ammonia solution and concentrated under reduced pressure to give the free base. This was purified by column chromatography over silica gel, eluting with 19:1:0.1/dichloromethane:methanol:ammonia and further purified by reverse-phase hplc (75:25 to 5:95/0.1% aqueous ammonium acetate:acetonitrile) to afford the title compound as an oil (0.051 g).

MS (APCI+ve) 421/423 (M+H)$^+$ $^1$H NMR (CDCl$_3$) δ 7.66 (1H, d); 7.38 (1H, d); 7.31 (1H dd); 6.68 (1H, t, br); 4.52 (2H, s); 3.72 (2H, t); 3.63 (2H, t); 3.17 (2H, d); 2.95 (2H, t); 2.85 (2H, t); 2.01 (3H, s, br); 1.91 (2H, s); 1.75-1.63 (6H, m); 1.59 (6H, s).

EXAMPLE 25

2-Chloro-5-[[2-[(3-hydroxypropyl)amino]ethoxy]methyl]-N-(tricyclo[3.3.1.1$^{3,7}$]dec-1-ylmethyl)-benzamide, acetic acid salt

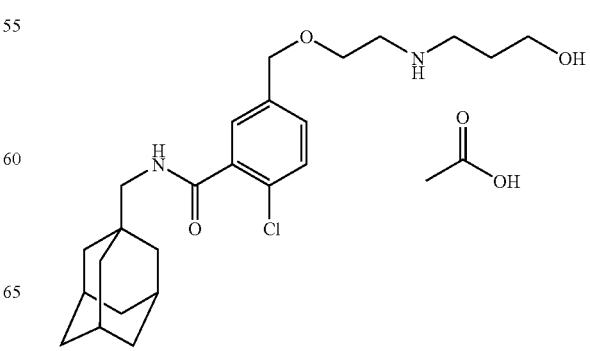

a) 2-Chloro-5-[(2-hydroxyethoxy)methyl]-N-(tricyclo[3.3.1.1$^{3,7}$]dec-1-ylmethyl)-benzamide A mixture of 5-(bromomethyl)-2-chloro-N-(2-tricyclo[3.3.1.1$^{3,7}$]dec-1-ylmethyl)-benzamide (Example 24a, 0.300 g), ethylene glycol (0.094 g) and silver trifluoroacetate (0.336 g) in dichloromethane (10 ml) was stirred under nitrogen at room temperature for 20 h. The solution was then decanted from the silver salts and the dichloromethane removed under vacuum. The crude material was purified on silica (eluting with ethyl acetate) to afford the subtitled compound as an oil (0.228 g).

MS (ESI+ve) MW 373/380 (M+H)$^+$ b) 2-Chloro-5-[[2-[(methylsulfonyl)oxy]ethoxy]methyl]-N-(tricyclo[3.3.1.1$^{3,7}$]dec-1-ylmethyl)-benzamide 2-Chloro-5-[(2-hydroxyethoxy)methyl]-N-(tricyclo[3.3.1.1$^{3,7}$]dec-1-ylmethyl)-benzamide (0.228 g, Example 25a) and triethylamine (0.21 ml) in dichloromethane (10 ml) were cooled to 5° C. under nitrogen and methanesulfonyl chloride (0.1 ml) was added. The mixture was stirred at room temperature for 20 h then poured into 2 N hydrochloric acid, and extracted into ethyl acetate. The combined extracts were washed with 2 N hydrochloric acid, saturated aqueous sodium hydrogencarbonate solution then brine, and dried over magnesium sulfate. The organics were filtered and concentrated under reduced pressure to afford the subtitled compound as a white solid (0.160 g).

$^1$H NMR (CDCl$_3$) δ 7.66 (1H, s); 7.41-7.33 (2H, m); 6.32 (1H, t, br); 4.57 (2H, s); 4.40-4.38 (2H, m); 3.77-3.75 (2H, m); 3.17-3.15 (2H, d); 3.04 (3H, s); 2.01 (3H, s, br); 1.75-1.64 (6H, m); 1.59 (6H, s, br).

c) 2-Chloro-5-[[2-[(3-hydroxypropyl)amino]ethoxy]methyl]-N-(tricyclo[3.3.1.1$^{3,7}$]dec-1-ylmethyl)-benzamide, acetic acid salt 2-Chloro-5-[[2-[(methylsulfonyl)oxy]ethoxy]methyl]-N-(tricyclo[3.3.1.1$^{3,7}$]dec-1-ylmethyl)-benzamide (0.160 g, Example 25b), 3-amino-1-propanol (0.27 ml) and n-butanol (4 ml) were heated together in a sealed tube at 110° C. for 24 h. The mixture was cooled, poured into 2 N sodium hydroxide solution and extracted into ethyl acetate. The extracts were dried over sodium sulfate, filtered and concentrated under reduced pressure. Chromatography over silica gel (eluting with 19:1:0.1/dichloromethane:methanol:ammonia) and further purification by reverse-phase HPLC (75:25 to 5:95/0.1% aqueous ammonium acetate:acetonitrile) afforded the title compound as a white solid (0.081 g).

MS (APCI+ve) 435/437 (M+H)$^+$ $^1$H NMR (CDCl$_3$) δ 7.75 (1H, s); 7.37 (1H, d); 7.27 (1H, d); 6.83 (1H, t, br); 4.56 (2H, s); 3.90 (4H, s, br); 3.21 (4H, s, br); 3.17 (2H, d); 2.01 (5H, s, br); 1.75-1.63 (6H, m); 1.59 (6H, s).

EXAMPLE 26

2-Chloro-5-[[[3-[(1-methylethyl)amino]propyl]amino]methyl]-N-(tricyclo[3.3.1.1$^{3,7}$]dec-1-ylmethyl)-benzamide

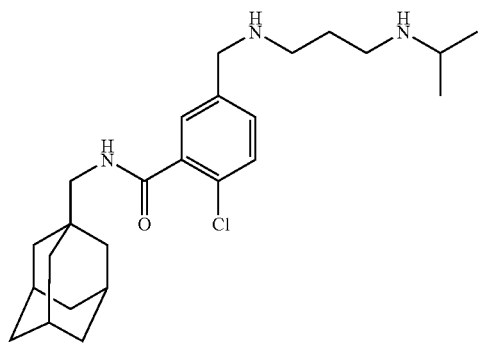

a) 5-Bromo-2-chloro-N-(tricyclo[3.3.1.1$^{3,7}$]dec-1-ylmethyl)-benzamide

To a suspension of 5-bromo-2-chlorobenzoic acid (5.00 g) in dichloromethane (25 ml) at 0° C. was added oxalyl chloride (3.7 ml) and DMF (5 drops). The resulting mixture was stirred at room temperature under a nitrogen atmosphere for 1 h, then concentrated under reduced pressure to yield a solid. The solid was dissolved in dichloromethane (20 ml) and added dropwise to a solution of 1-adamantanemethylamine (3.36 g) and N,N-diisopropylethylamine (5.55 ml) in dichloromethane (20 ml). The resulting solution was allowed to stir at room temperature under a nitrogen atmosphere for 20 h. The reaction mixture was diluted with dichloromethane and washed in sequence with water, 10% aqueous potassium carbonate solution, 10% aqueous potassium hydrogen sulfate and saturated brine. The organic phase was then dried over soidum sulfate, filtered and concentrated under reduced pressure to afford the subtitled compound as a solid (7.84 g).

MS (APCI+ve) 383/385 (M+H)$^+$ $^1$H NMR (DMSO-d$_6$) δ 8.42 (1H, t); 7.63 (1H, dd); 7.57 (1H, m); 7.45 (1H, d); 2.93 (2H, d); 1.94 (3H, s, br); 1.69-1.58 (6H, m); 1.51 (6H, s).

b) 2-Chloro-5-formyl-N-(tricyclo[3.3.1.1$^{3,7}$]dec-1-ylmethyl)-benzamide

A solution of 5-bromo-2-chloro-N-(tricyclo[3.3.1.1$^{3,7}$]dec-1-ylmethyl)-benzamide (3.25 g, Example 25a) in tetrahydrofuran (150 ml) was cooled to −78° C. under a nitrogen atmosphere. A solution of 1.4 M methyllithium in diethyl ether (6.1 ml) was added to this solution over 2 min. The mixture was stirred at −78° C. for 10 min, then a 1.7 M solution of tert-butyllithium in pentane (10.0 ml) was added dropwise. The mixture was stirred at −78° C. for a further 10 min, then dimethylformamide (1.0 ml) was added. The resulting solution was stirred at −78° C. for 30 min, quenched with saturated aqueous ammonium chloride solution (100 ml) and extracted with ethyl acetate. The combined extracts were dried over sodium sulfate, filtered, and the filtrate concentrated under reduced pressure to give the subtitled compound as a solid (2.76 g).

MS (APCI+ve) 332/324 (M+H)$^+$ $^1$H NMR (DMSO-d$_6$) δ 10.04 (1H, s); 8.49 (1H, t); 7.96-7.91 (2H, m); 7.74 (1H, d); 2.96 (2H, d); 1.95 (3H, s); 1.64 (6H, m); 1.53 (6H, d).

c) 2-Chloro-5-[[[3-[(1-methylethyl)amino]propyl]amino]methyl]-N-(tricyclo[3.3.1.1$^{3,7}$]dec-1-ylmethyl)-benzamide A mixture of 2-chloro-5-formyl-N-(tricyclo[3.3.1.1$^{3,7}$]dec-1-ylmethyl)-benzamide (0.244 g, Example 25b), N-isopropyl-1,3-propanediamine (0.211 g), p-toluenesulfonic acid (0.005 g) and toluene (30 ml) were refluxed together under Dean-Stark conditions for 3 h. The mixture was cooled and concentrated under reduced pressure to an oil. This was dissolved in ethanol (30 ml) and cooled to 0° C. under a nitrogen atmosphere. Solid sodium borohydride (0.040 g) was added portionwise and the mixture stirred at room temperature for 30 min, then concentrated under reduced pressure and the residue purified by column chromatography over silica (eluting with 9:1:0.1 dichloromethane/methanol/35% aqueous ammonia) to give the title compound (0.015 g) and a by-product (see Example 27).

MS (APCI+ve) 432/434 (M+H)$^+$ $^1$H NMR (CDCl$_3$) δ 7.64 (1H, s); 7.37-7.32 (2H, m); 6.28 (1H s, br); 3.78 (2H, s); 3.18 (2H, d); 2.84-2.74 (1H, m); 2.70-2.64 (4H, m); 2.01 (3H, s, br); 1.76-1.63 (8H, m); 1.59 (6H, s, br); 1.05 (6H, d).

EXAMPLE 27

5-[[(3-Aminopropyl)amino]methyl]-2-chloro-N-(tricyclo[3.3.1.1³,⁷]dec-1-ylmethyl)-benzamide

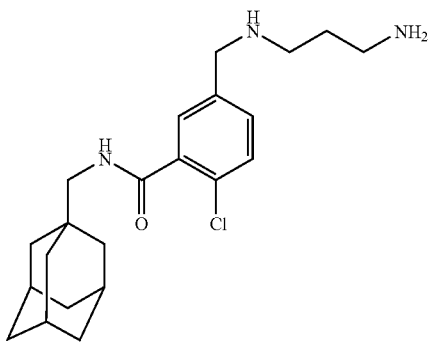

Formed as a by-product in Example 26c above (0.125 g).

MS (APCI+ve) 390/392 (M+H)⁺

¹H NMR (CDCl₃) δ 7.65 (1H, s); 7.37-7.32 (2H, m); 6.31 (1H, t, br); 3.79 (2H, s); 3.18 (2H, d); 2.77 (2H, t); 2.68 (2H, t); 2.01 (3H, s, br); 1.75-1.61 (8H, m); 1.59 (6H, s, br).

EXAMPLE 28

2-Chloro-5-[[[2-[(1-methylethyl)amino]ethyl]amino]methyl]-N-(tricyclo[3.3.1.1³,⁷]dec-1-ylmethyl)-benzamide

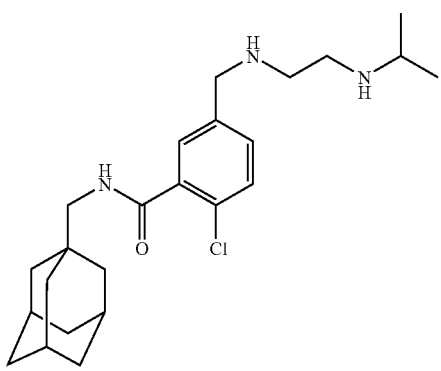

Synthesised as in Example 26 using 2-chloro-5-formyl-N-(tricyclo[3.3.1.1³,⁷]dec-1-ylmethyl)-benzamide (0.500 g, Example 25b) and N-isopropylethylenediamine (0.186 g) to give the title compound as a solid (0.105 g).

MS (APCI+ve) 418/420 (M+H)⁺

¹H NMR (CDCl₃) δ 7.65 (1H, s); 7.34 (2H, s); 6.26 (1H, t, br); 3.79 (2H, s); 3.18 (2H, d); 2.79-2.69 (5H, m); 2.01 (3H, s, br); 1.75-1.64 (6H, m); 1.59 (6H, s, br); 1.50 (2H, s, br), 1.05 (6H, d).

EXAMPLE 29

3-[[3-[4-Chloro-3-[[(tricyclo[3.3.1.1³,⁷]dec-1-ylmethyl)amino]carbonyl]phenyl]-propyl]amino]propanoic acid, 2,2-dimethylpropyl ester, trifluoroacetic acid salt

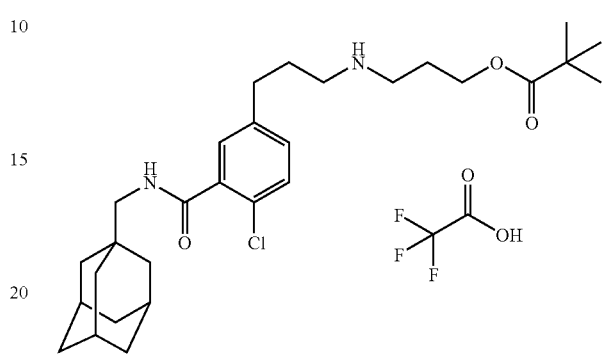

a) 2-Chloro-5-iodo-N-(tricyclo[3.3.1.1³,⁷]dec-1-ylmethyl)-benzamide

2-Chloro-5-iodobenzoic acid (10.0 g) was suspended in dichloromethane (160 ml) then oxalyl chloride (4.0 ml) was added followed by N,N-dimethylformamide (40 µl). After 24 h the solvent was evaporated to afford a white solid, which was then redissolved in dichloromethane (160 ml). Triethylamine (14.8 ml) was added, followed by adamantane methylamine (6.9 ml) with cooling to keep the temperature below 30° C. The resulting slightly cloudy mixture was stirred for 1 h, then solvent was evaporated to give a pale yellow solid. The solid was stirred in a mixture of ethyl acetate (400 ml) and 2 M hydrochloric acid (300 ml) until the solid dissolved to afford two clear phases. The (upper) organic phase was separated off and washed with 2 M sodium hyroxide solution (300 ml), then dried (Na₂SO₄) and evaporated to a yellow solid. The solid was suspended in iso-hexane (100 ml), then filtered and washed with more iso-hexane (40 ml), and the resulting off-white solid dried in vacuo at 40° C. to afford the subtitled compound (14.0 g).

MS (APCI+ve) 430/432 (M+H)⁺

¹H NMR (CDCl₃) δ 8.00 (1H, d); 7.66 (1H, dd); 7.14 (1H, d); 6.17 (1H, s, br); 3.17 (2H, d); 2.01 (3H, s); 1.69 (6H, q); 1.58 (6H, d).

b) 2-Chloro-5-(3-oxopropyl)-N-(tricyclo[3.3.1.1³,⁷]dec-1-ylmethyl)-benzamide

2-Chloro-5-iodo-N-(tricyclo[3.3.1.1³,⁷]dec-1-ylmethyl)-benzamide (5.00 g Example 29a), tetrabutylammonium chloride (3.40 g) and sodium hydrogencarbonate (2.44 g) were charged to a flask, followed by Pd(OAc)₂ (53.3 mg), toluene (50 ml) and allyl alcohol (1.01 ml). The pale brown mixture was heated at 80° C. for 5 h, then cooled to ambient temperature. The mixture was filtered and the residues washed with additional toluene (50 ml+50 ml). The combined toluene solutions were washed with water (100 ml), then dried over MgSO₄ and evaporated to a light brown solid (3.82 g).

MS (APCI+ve) 360/362 (M+H)⁺

¹H NMR (CDCl₃) δ 9.81 (1H, s); 7.56 (1H, s); 7.32 (1H, d); 7.19 (1H, d); 6.28 (1H, s, br); 3.18 (2H, d); 2.96 (2H, t); 2.81 (2H, t); 2.01 (3H, s); 1.70 (6H, q); 1.58 (6H, s).- c) 2-Chloro-5-[3-[(3-hydroxypropyl)amino]propyl]-N-(tricyclo[3.3.1.1$^{3,7}$]dec-1-ylmethyl)-benzamide Sodium triacetoxyborohydride (1.86 g) was added to a solution of 2-chloro-5-(3-oxopropyl)-N-(tricyclo[3.3.1.1$^{3,7}$]dec-1-ylmethyl)-benzamide (1.57 g, Example 29b) and 3-amino-1-propanol (0.8 ml) in dichloromethane (150 ml). After 24 h the crude reaction mixture was purified by chromatography (eluting with 5-20% methanol in dichloromethane+1% ammonia) to give the subtitled compound as a white solid (1.05 g).

MS (APCI+ve) 419/421 (M+H)$^+$ d) 3-[[3-[4-Chloro-3-[[(tricyclo[3.3.1.1$^{3,7}$]dec-1-ylmethyl)amino]carbonyl]-phenyl]propyl][(1,1-dimethylethoxy)carbonyl]amino]propanoic acid, 2,2-dimethylpropyl ester 2-Chloro-5-[3-[(3-hydroxypropyl)amino]propyl]-N-(tricyclo[3.3.1.1$^{3,7}$]dec-1-ylmethyl)-benzamide (0.271 g, Example 29c), N,N-diisopropylethylamine (0.50 ml) and tetrahydrofuran (10 ml) were stirred together under nitrogen. Trimethylacetyl chloride (0.26 ml) was added dropwise and the mixture stirred at room temperature for 48 h, then poured into water and extracted into ethyl acetate. The combined extracts were dried over sodium sulfate, filtered, concentrated under reduced pressure and chromatographed over silica (eluting with 4:1 isohexane/ethyl acetate) to give the subtitled compound (0.158 g) as an oil.

MS (ESI+ve) 603/605 (M+H)$^+$ e) 3-[[3-[4-Chloro-3-[[(tricyclo[3.3.1.1$^{3,7}$]dec-1-ylmethyl)amino]carbonyl]-phenyl]propyl]amino]propanoic acid, 2,2-dimethylpropyl ester, trifluoroacetic acid salt 3-[[3-[4-Chloro-3-[[(tricyclo[3.3.1.1$^{3,7}$]dec-1-ylmethyl)amino]carbonyl]-phenyl]propyl][(1,1-dimethylethoxy)carbonyl]amino]propanoic acid, 2,2-dimethylpropyl ester (0.158 g, Example 29d), trifuoroacetic acid (2 ml) and dichloromethane (2 ml) were stirred together under nitrogen for 15 min, then concentrated under reduced pressure to give the title compound (0.170 g).

MS (APCI+ve) 503/505 (M+H)$^+$ $^1$H NMR (CDCl$_3$) δ 7.40 (1H, d); 7.32 (1H, d); 7.14 (1H dd); 4.12 (2H, t); 3.16 (2H, d); 3.09-2.89 (4H, m); 2.64 (2H, t); 2.06-1.92 (7H, m); 1.75-1.63 (6H, m); 1.58 (6H, s); 1.18 (9H, s).

EXAMPLE 30

5-(2-Aminoethyl)-2-chloro-N-(tricyclo[3.3.1.1$^{3,7}$]dec-1-ylmethyl)benzamide

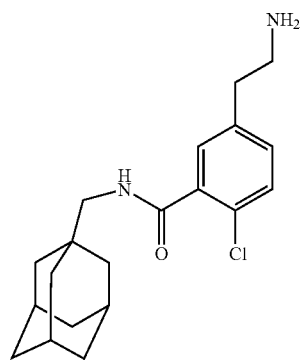

a) 2-Chloro-5-(cyanomethyl)-N-(tricyclo[3.3.1.1$^{3,7}$]dec-1-ylmethyl)benzamide Potassium cyanide (525 mg) and 18-crown-6 (150 mg) were added to a solution of 5-(bromomethyl)-2-chloro-N-(2-tricyclo[3.3.1.1$^{3,7}$]dec-1-ylmethyl)-benzamide (Example 24a, 1.8 g) in ethanol (50 ml) and the mixture heated under reflux for 24 h. On cooling the reaction mixture was evaporated to dryness and the residue partitioned between ethyl acetate and saturated sodium hydrogencarbonate solution. The organics were separated, washed with brine, dried over magnesium sulfate, filtered and evaporated. Purification by chromatography on silica (eluting with a gradient of isohexane/ethyl acetate/4:1 to 6:4) gave the subtitled product as a pink solid (1.0 g).

MS (APCI+ve) 343/345 (M+H)$^+$ $^1$H NMR (DMSO-$_6$) δ 8.38 (1H, t); 7.52 (1H, d); 7.43-7.38 (2H, m); 4.08 (2H, s); 2.94 (2H, d); 1.92 (3H, s); 1.63 (6H, q); 1.52 (6H, s).

b) [2-[4-Chloro-3-[[(tricyclo[3.3.1.1$^{3,7}$]dec-1-ylmethyl)amino]carbonyl]phenyl]-ethyl]carbamic acid, 1,1-dimethylethyl ester Sodium borohydride (1.6 g) was added portionwise to a cooled solution of 2-chloro-5-(cyanomethyl)-N-(tricyclo[3.3.1.1$^{3,7}$]dec-1-ylmethyl)benzamide (Example 30a, 2.1 g), (1,1-dimethylethoxy)carbonyl carbonic acid, 1,1-dimehtylethyl ester (2.67 g) and cobalt(II)chloride (1.6 g) in methanol (100 ml). After 1.5 h the solvent was evaporated and the residue slurried between ethyl acetate and saturated sodium hyrogencarbonate solution and the insoluble cobalt salts filtered. The organic phase was separated and washed with brine, dried over sodium sulfate, filtered and evaporated to give the subtitled product as a foam (2.2 g).

MS (APCI+ve) 447/449 (M+H)$^+$ $^1$H NMR (CDCl$_3$) δ 7.54 (1H, d); 7.34 (1H, d); 7.19 (1H, dd); 6.28 (1H, s, br); 4.54 (1H, s, br); 3.39 (2H, q); 3.18 (2H, d); 2.80 (2H, t); 2.04 (3H, s); 1.70 (6H, q); 1.64 (6H, s); 1.42 (9H, s).

c) 5-(2-Aminoethyl)-2-chloro-N-(tricyclo[3.3.1.1$^{3,7}$]dec-1-ylmethyl)benzamide, hydrochloride salt Hydrochloric acid (4 M in 1,4-dioxane, 3.0 ml) was added to a solution of [2-[4-chloro-3-[[(tricyclo[3.3.1.1]dec-1-ylmethyl)amino]carbonyl]phenyl]ethyl]carbamic acid, 1,1-dimethylethyl ester (2.2 g, Example 30b) in methanol/dichloromethane (1:1) (50 ml). After 24 h the solvent was evaporated to leave the title compound as a foam (1.85 g).

MS (APCI+ve) 347/349 (M+H)$^+$ $^1$H NMR (DMSO-d$_6$) δ 8.31 (1H, t); 8.15 (3H, s, br); 7.43 (1H, d); 7.31 (2H, m); 3.05-2.98 (2H, m); 2.95-2.85 (4H, m); 1.94 (3H, s); 1.63 (6H, q); 1.52 (6H, s).

EXAMPLE 31

2-Chloro-5-[3-[(2-hydroxyethyl)pentylamino]propyl]-N-(tricyclo[3.3.1.1$^{3,7}$]dec-1-ylmethyl) benzamide

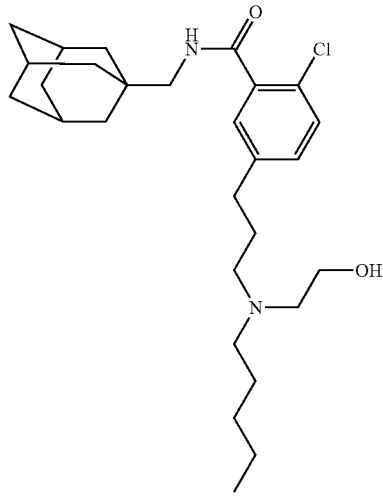

Prepared according to the procedure described in Example 6f
MS (APCI+ve) 475/477 (M+H)$^+$

EXAMPLE 32

2-Chloro-5-[3-(methyl-2-propenylamino)propyl]-N-(tricyclo[3.3.1.1$^{3,7}$]dec-1-ylmethyl)-benzamide

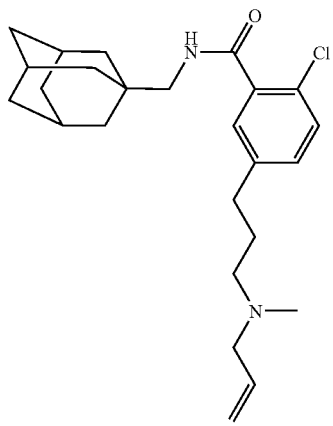

Prepared according to the procedure described in Example 6f.
MS (APCI+ve) 415/417 (M+H)$^+$

EXAMPLE 33

2-Chloro-5-[3-[[2-(dimethylamino)ethyl]methylamino]propyl]-N-(tricyclo[3.3.1.1$^{3,7}$]dec-1-ylmethyl)-benzamide

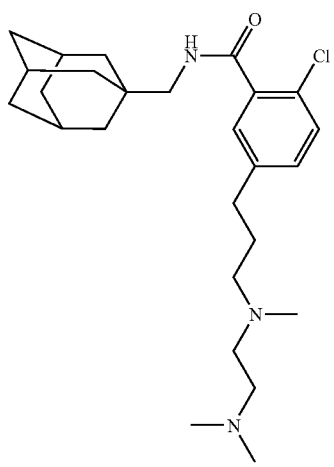

Prepared according to the procedure described in Example 6f.
MS(APCI+ve) 446/448 (M+H)$^+$

EXAMPLE 34

5-[3-(Butylethylamino)propyl]-2-chloro-N-(tricyclo[3.3.1.1$^{3,7}$]dec-1-ylmethyl)-benzamide

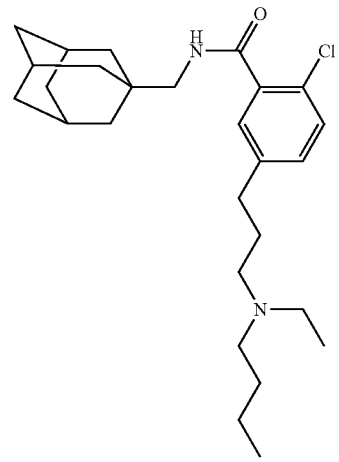

Prepared according to the procedure described in Example 6f.
MS (APCI+ve) 445/447 (M+H)$^+$

EXAMPLE 35

2-Chloro-5-[3-(methylpentylamino)propyl]-N-(tricyclo[3.3.1.1$^{3,7}$]dec-1-ylmethyl)-benzamide

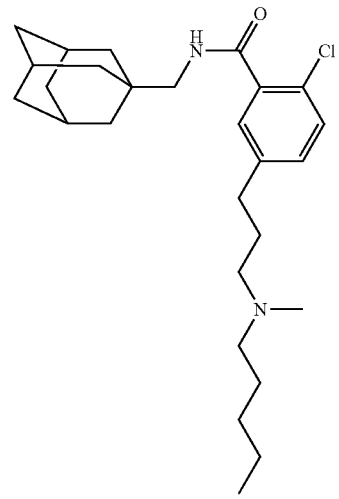

Prepared according to the procedure described in 6f.
MS (APCI+ve) 445/447 (M+H)$^+$

EXAMPLE 36

2-Chloro-5-[3-[[2-(diethylamino)ethyl]propyl]-N-(tricyclo[3.3.1.1³,⁷]dec-1-ylmethyl)-benzamide

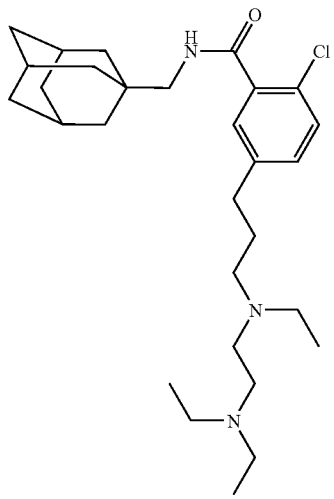

Prepared according to the procedure described in Example 6f.

MS (APCI+ve) 488/490 (M+H)⁺

EXAMPLE 37

2-Chloro-5-[3-[(2-hdyroxyethyl)methylamino]propyl]-N-(tricyclo[3.3.1.1³,⁷]dec-1-ylmethyl)-benzamide

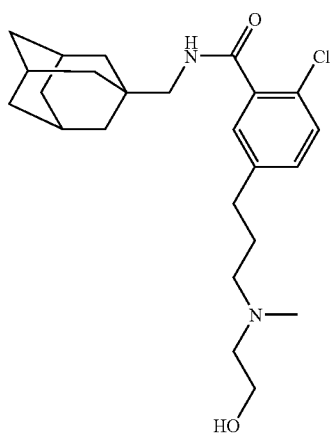

Prepared according to the procedure described in Example 6f.

MS (APCI+ve) 419/421 (M+H)⁺

EXAMPLE 38

2-Chloro-5-[3-(dipropylamino)propyl]-N-(tricyclo[3.3.1.1³,⁷]dec-1-ylmethyl)-benzamide

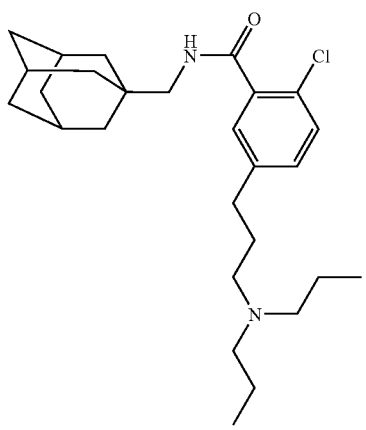

Prepared according to the procedure described in Example 6f.

MS (APCI+ve) 445/447 (M+H)⁺

EXAMPLE 39

2-Chloro-5-[3-[(2-hydroxyethyl)(1-methylethyl)amino]propyl]-N-(tricyclo[3.3.1.1³,⁷]dec-1-ylmethyl)-benzamide

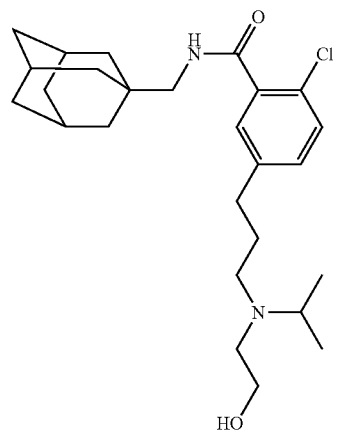

Prepared according to the procedure described in Example 6f.

MS (APCI+ve) 447/449 (M+H)⁺

EXAMPLE 40

5-[3-[Butyl(2-hydroxyethyl)amino]propyl]-2-chloro-N-(tricyclo[3.3.1.1³,⁷]dec-1-ylmethyl)-benzamide

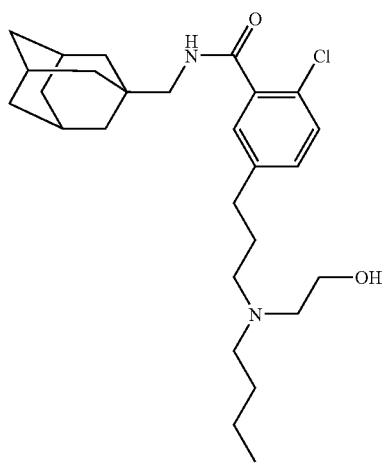

Prepared according to the procedure described in Example 6f.

MS (APCI+ve) 461/463 (M+H)⁺

EXAMPLE 41

2-Chloro-5-[3-(diethylamino)propyl]-N-(tricyclo[3.3.1.1³,⁷]dec-1-ylmethyl)-benzamide

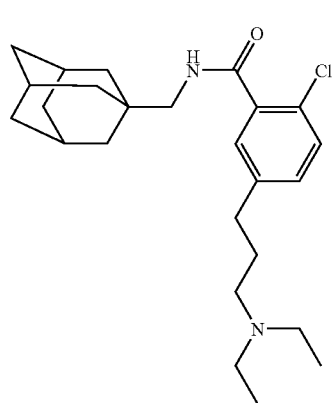

Prepared according to the procedure described in Example 6f.

MS (APCI+ve) 417/419 (M+H)⁺

EXAMPLE 42

2-Chloro-5-[3-(dimethylamino)propyl]-N-(tricyclo[3.3.1.1³,⁷]dec-1-ylmethyl)-benzamide

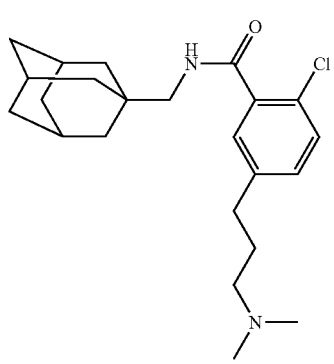

Prepared according to the procedure descried in Example 6f.

MS (APCI+ve) 389/391 (M+H)⁺

EXAMPLE 43

5-[3-(Buthylmethylamino)propyl]-2-chloro-N-(tricyclo[3.3.1.1³,⁷]dec-1-ylmethyl)-benzamide

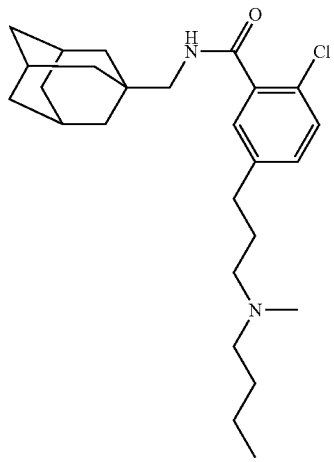

Prepared according to the procedure described in Example 6f.

MS (APCI+ve) 431/433 (M+H)⁺

EXAMPLE 44

2-Chloro-5-[3-[(2-hydroxyethyl)propylamino]pro-pyl]-N-(tricyclo[3.3.1.1$^{3,7}$]dec-1-ylmethyl)-benzamide

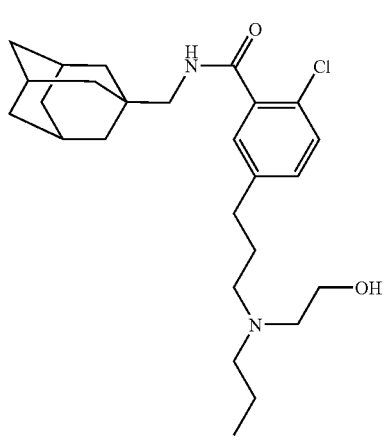

Prepared according to the procedure described in Example 6f.

MS (APCI+ve) 447/449 (M+H)$^+$

EXAMPLE 45

2-Chloro-5-[3-[ethyl(2-hydroxyethyl)amino]propyl]-N-(tricyclo[3.3.1.1$^{3,7}$]dec-1-ylmethyl)-benzamide

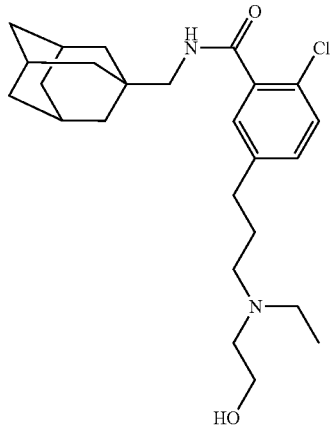

Prepared according to the procedure described in Example 6f.

MS (APCI+ve) 433/435 (M+H)$^+$

EXAMPLE 46

2-Chloro-5-[3-(dibutylamino)propyl]-N-(tricyclo[3.3.1.1$^{3,7}$]dec-1-ylmethyl)-benzamide

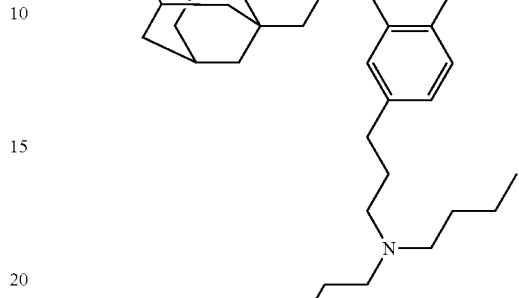

Prepared according to the procedure described in Example 6f.

MS (APCI+ve) 473/475 (M+H)$^+$

EXAMPLE 47

2-Chloro-5-[3-(ethylpropylamino)propyl]-N-(tricyclo[3.3.1.1$^{3,7}$]dec-1-ylmethyl)-benzamide

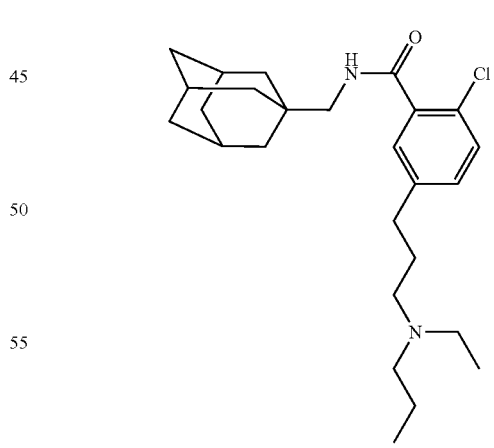

Prepared according to the procedure described in Example 6f.

MS (APCI+ve) 431/433 (M+H)$^+$

EXAMPLE 48

2-Chloro-5-[3-[methyl(1-methylethyl)amino]propyl]-N-(tricyclo[3.3.1.1³,⁷]dec-1-ylmethyl)-benzamide

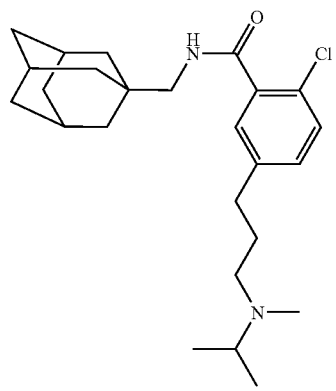

Prepared according to the procedure described in Example 6f.

MS (APCI+ve) 417/419 (M+H)⁺

EXAMPLE 49

2-Chloro-5-[3-[[3-(dimethylamino)propyl]methylamino]propyl]-N-(tricyclo[3.3.1.1³,⁷]dec-1-ylmethyl)-benzamide

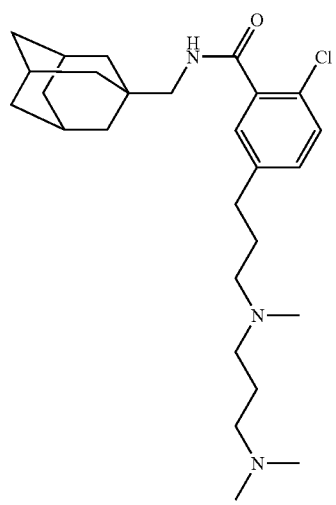

Prepared according to the procedure described in Example 6f.

MS (APCI+ve) 460/462 (M+H)⁺

EXAMPLE 50

2-Chloro-5-[3-[cyclohexyl(2-hydroxyethyl)amino]propyl]-N-(tricyclo[3.3.1.1³,⁷]dec-1-ylmethyl)-benzamide

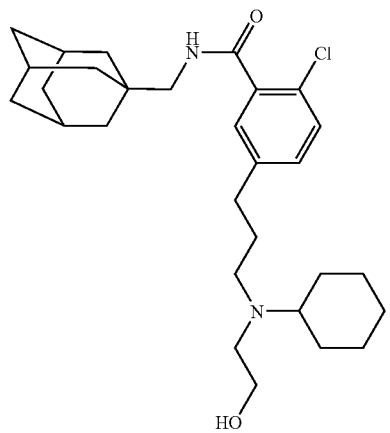

Prepared according to the procedure described in Example 6f.

MS (APCI+ve) 487/489 (M+H)⁺

EXAMPLE 51

2-Chloro-5-[3-(cyclohexylmethylamino)propyl]-N-(tricyclo[3.3.1.1³,⁷]dec-1-ylmethyl)-benzamide

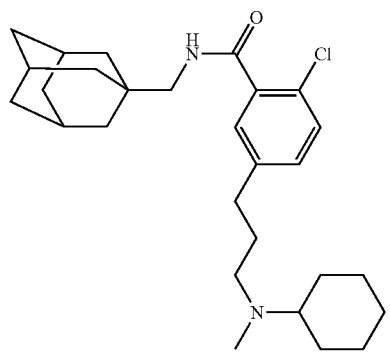

Prepared according to the procedure described in Example 6f.

MS (APCI+ve) 457/459 (M+H)⁺

EXAMPLE 52

2-Chloro-5-[3-(cyclohexylamino)propyl]-N-(tricyclo[3.3.1.1^{3,7}]dec-1-ylmethyl)-benzamide

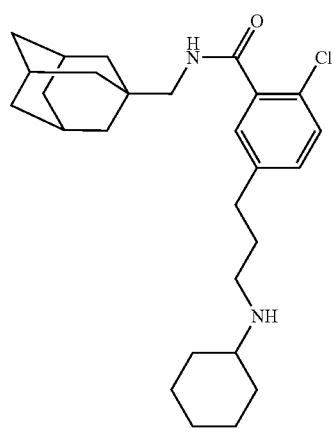

Prepared according to the procedure described in Example 6f.

MS (APCI+ve) 443/445 (M+H)^{+}

EXAMPLE 53

2-Chloro-5-[3-[[1-(hydroxymethyl)-2,2-dimethylpropyl]amino]propyl]-N-(tricyclo[3.3.1.1^{3,7}]dec-1-ylmethyl)-benzamide

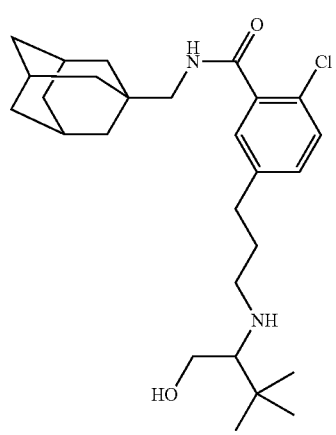

Prepared according to the procedure described in Example 6f.

MS (APCI+ve) 461/463 (M+H)^{+}

EXAMPLE 54

2-Chloro-5-[3-(cyclopropylamino)propyl]-N-(tricyclo[3.3.1.1^{3,7}]dec-1-ylmethyl)-benzamide

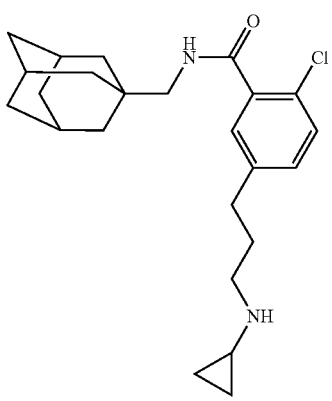

Prepared according to the procedure described in Example 6f.

MS (APCI+ve) 401/403 (M+H)^{+}

EXAMPLE 55

2-Chloro-5-[3-[[2-(dimethylamino)ethyl]amino]propyl]-N-(tricyclo[3.3.1.1^{3,7}]dec-1-ylmethyl)-benzamide

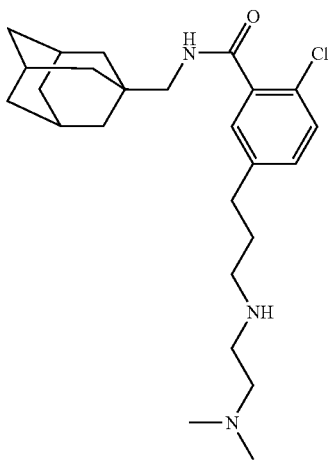

Prepared according to the procedure described in Example 6f.

MS (APCI+ve) 432/434 (M+H)^{+}

EXAMPLE 56

2-Chloro-5-[3-[(3-hydroxy-2,2-dimethylpropyl)amino]propyl]-N-(tricyclo[3.3.1.1$^{3,7}$]dec-1-ylmethyl)-benzamide

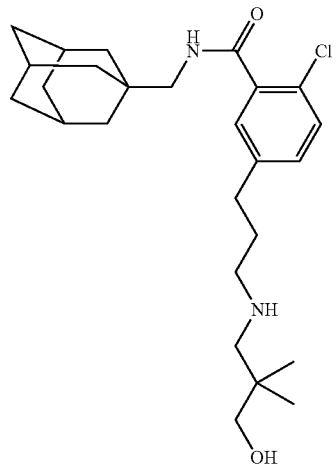

Prepared according to the procedure described in Example 6f.

MS (APCI+ve) 447/449 (M+H)$^+$

EXAMPLE 57

2-Chloro-5-[3-[(1,1-dimethylethyl)amino]propyl]-N-(tricyclo[3.3.1.1$^{3,7}$]dec-1-ylmethyl)-benzamide

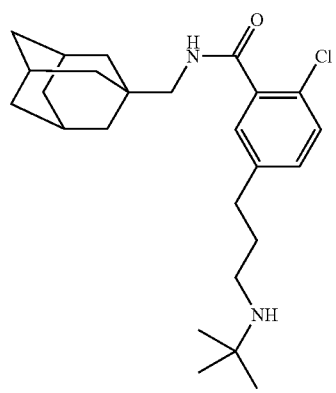

Prepared according to the procedure described in Example 6f.

MS (APCI+ve) 417/419 (M+H)$^+$

EXAMPLE 58

2-Chloro-5-[3-[[3-(dimethylamino)propyl]amino]propyl]-N-(tricyclo[3.3.1.1$^{3,7}$]dec-1-ylmethyl)-benzamide

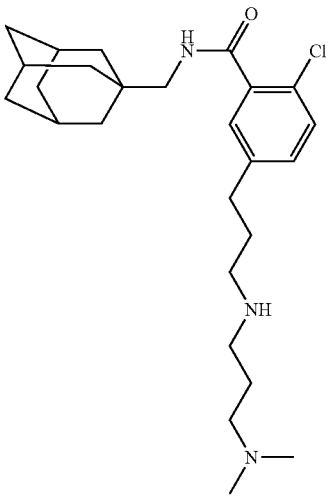

Prepared according to the procedure described in Example 6f.

MS (APCI+ve) 446/448 (M+H)$^+$

EXAMPLE 59

2-Chloro-5-[3-(cyclopentylamino)propyl]-N-(tricyclo[3.3.1.1$^{3,7}$]dec-1-ylmethyl)-benzamide

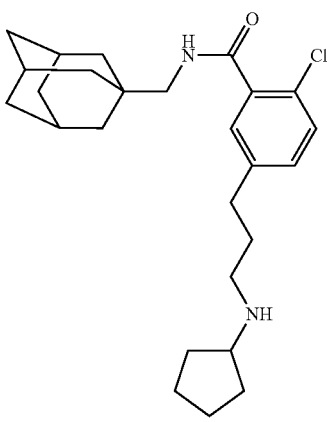

Prepared according to the procedure described in Example 6f.

MS (APCI+ve) 429/431 (M+H)$^+$

EXAMPLE 60

2-Chloro-N-(tricyclo[3.3.1.1$^{3,7}$]dec-1-ylmethyl)-5-[3-[(1,2,2-trimethylpropyl)amino]propyl]-benzamide

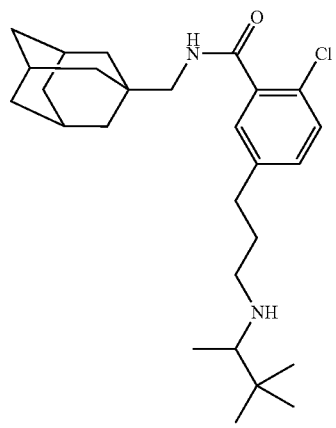

Prepared according to the procedure described in Example 6f.

MS (APCI+ve) 445/447 (M+H)$^+$

EXAMPLE 61

5-[3-(Butylamino)propyl]-2-chloro-N-(tricyclo[3.3.1.1$^{3,7}$]dec-1-ylmethyl)-benzamide

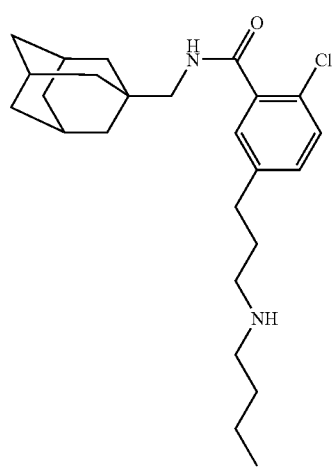

Prepared according to the procedure described in Example 6f.

MS (APCI+ve) 417/419 (M+H)$^+$

EXAMPLE 62

2-Chloro-5-[3-[[1-(hydroxymethyl)-2-methylpropyl]amino]propyl]-N-(tricyclo[3.3.1.1$^{3,7}$]dec-1-ylmethyl)-benzamide

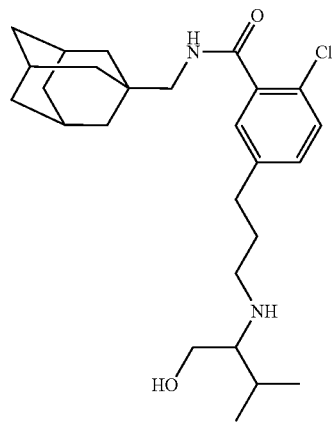

Prepared according to the procedure described in Example 6f.

MS (APCI+ve) 447/449 (M+H)$^+$

EXAMPLE 63

2-Chloro-5-[3-[(1-methylpropyl)amino]propyl]-N-(tricyclo[3.3.1.1$^{3,7}$]dec-1-ylmethyl)-benzamide

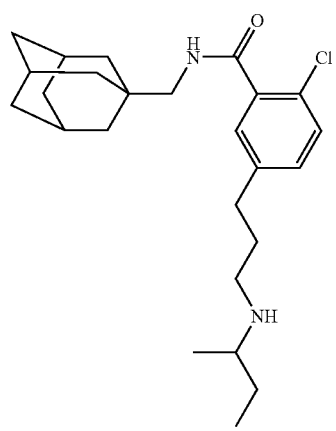

Prepared according to the procedure described in Example 6f.

MS (APCI+ve) 417/419 (M+H)$^+$

EXAMPLE 64

2-Chloro-5-[3-[[2-(methylthio)ethyl]amino]propyl]-N-(tricyclo[3.3.1.1^{3,7}]dec-1-ylmethyl)-benzamide

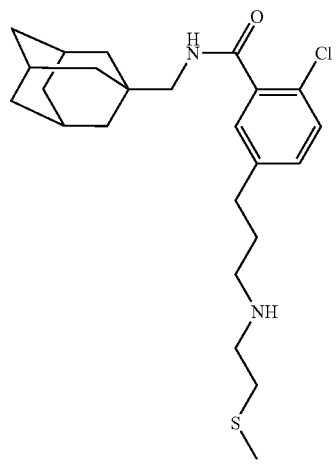

Prepared according to the procedure described in Example 6f.

MS (APCI+ve) 435/437 (M+H)+

EXAMPLE 65

2-Chloro-5-[3-[(2-hydoxy-1,1-dimethylethyl)amino]propyl]-N-(tricyclo[3.3.1.1^{3,7}]dec-1-ylmethyl)-benzamide

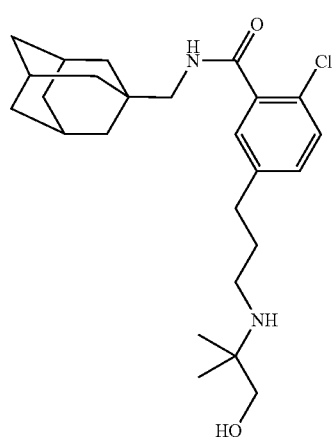

Prepared according to the procedure described in Example 6f.

MS (APCI+ve) 433/435 (M+H)+

EXAMPLE 66

2-Chloro-5-[3-[(cyclohexylmethyl)amino]propyl]-N-(tricyclo[3.3.1.1^{3,7}]dec-1-ylmethyl)-benzamide

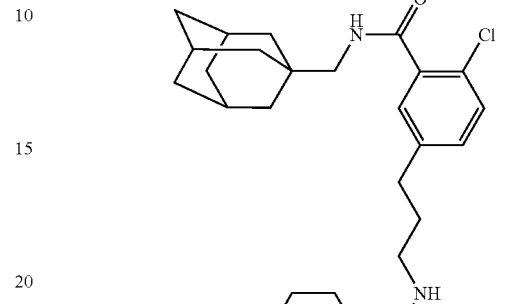

Prepared according to the procedure described in Example 6f.

MS (APCI+ve) 457/459 (M+H)+

EXAMPLE 67

2-Chloro-5-[3-(2-propenylamino)propyl]-N-(tricyclo[3.3.1.1^{3,7}]dec-1-ylmethyl)-benzamide

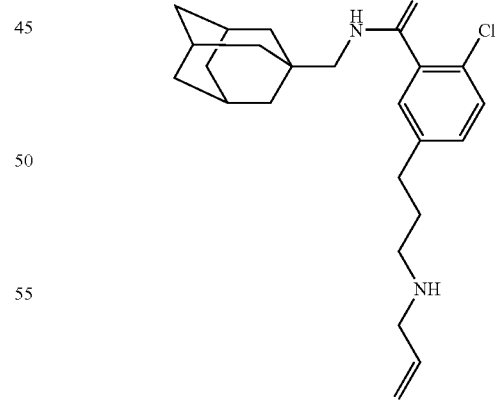

Prepared according to the procedure described in Example 6f.

MS (APCI+ve) 401/403 (M+H)+

EXAMPLE 68

2-Chloro-5-[3-[(2-fluoroethyl)amino]propyl]-N-(tricyclo[3.3.1.1³,⁷]dec-1-ylmethyl)-benzamide

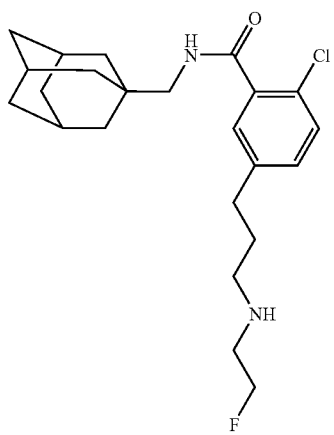

Prepared according to the procedure described in Example 6f.

MS (APCI+ve) 407/409 (M+H)⁺

EXAMPLE 69

2-Chloro-5-[3-[(2-methoxy-1-methylethyl)amino]propyl]-N-(tricyclo[3.3.1.1³,⁷]dec-1-ylmethyl)-benzamide

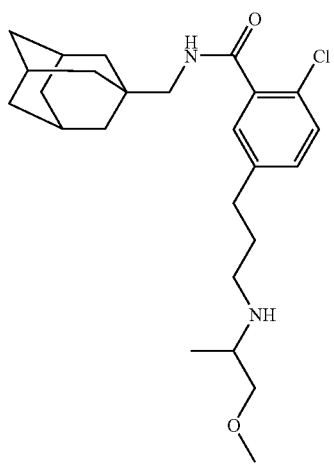

Prepared according to the procedure described in Example 6f.

MS (APCI+ve) 433/435 (M+H)⁺

EXAMPLE 70

2-Chloro-5-[3-[3-(methylamino)propoxy]propyl]-N-(tricyclo[3.3.1.1³,⁷]dec-1-ylmethyl)benzamide, dihydrochloride salt a) 2-Chloro-5-(3-iodopropyl)-N-(tricyclo[3.3.1.1³,⁷]dec-1-ylmethyl) benzamide 2-Chloro-5-(3-hydroxypropyl)-N-(tricyclo[3.3.1.1³,⁷]dec-1-ylmethyl)-benzamide (5.9 g, Example 6d), iodine (6.2 g, 24.4 mmol), triphenylphosphine (6.4 g, 24.4 mmol) and imidazole (1.66 g, 24.4 mmol) were stirred in dichloromethane (100 ml) at room temperature for 1 h. The reaction was quenched with sat. aq. $Na_2S_2O_3$ and the layers were separated. The aqueous phase was extracted with ethyl acetate. The combined organic phases were dried ($Na_2SO_4$), concentrated and purified by column chromatography on silica (eluting with EtOAc:isohexane/1:3) to afford the subtitled compound as a pale yellow solid (6.8 g)

MS (APCI+ve) 472/474 (M+H)⁺ b) 2-Chloro-5-[3-[3-(methylamino)propoxy]propyl]-N-(tricyclo[3.3.1.1³,⁷]dec-1-ylmethyl)benzamide, dihydrochloride salt Silver trifluoroacetate (0.7 g, 3.2 mmol) was added to 1,1-dimethylethyl (3-hydroxypropyl)methyl carbamic acid (1.8 g, 9.5 mmol) [Synth. Commun. (1995), 25(14), 2135-43] in dichloromethane (20 ml). After 10 min. 2-chloro-5-(3-iodopropyl)-N-(tricyclo[3.3.1.1³,⁷]dec-1-ylmethyl) benzamide (1.0 g, Example 70a) was added and the mixture was stirred for 24 h. The resulting mixture was washed with water and concentrated. Treatment with 4 M hydrochloric acid in 1,4-dioxane/methanol, concentration and purification by RPHPLC gave the title compound (26 mg) as a white solid.

MS (APCI+ve) 433/435 (M+H)⁺

¹H NMR (DMSO-$d_6$) 8.79-8.35 (1H, m); 8.29 (1H, t, J=6.2 Hz), 7.38 (1H, d, J=8.1 Hz), 7.31-7.14 (m, 2H), 3.48-3.31 (4H, m), 2.98-2.81 (4H, m), 2.63 (2H, t, J=7.6 Hz), 2.50 (3H, s), 1.94 (3H, s), 1.87-1.73 (4H, m), 1.64 (6H, m), 1.52 (6H, m)

EXAMPLE 71

5-[[[(1-Aminocyclopropyl)methyl](2-hydroxyethyl)amino]methyl]-2-chloro-N-(tricyclo[3.3.1.1$^{3,7}$]dec-1-ylmethyl)-benzamide

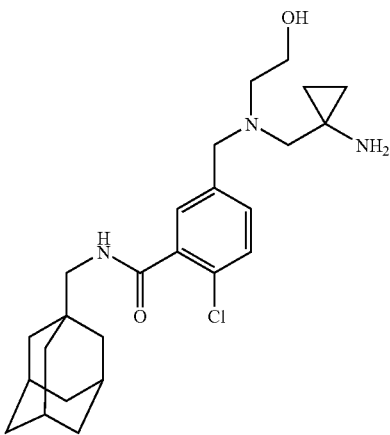

a) 5-Bromomethyl-2-chloro-benzoic acid

To a stirred solution of 2-chloro-5-methyl-benzoic acid (25 g) in chloroform (500 ml) at 50° C. was added N-bromosuccinimide (27.40 g). The flask was purged with nitrogen and azobisisobutyronitrile (0.10 g) was added in one portion. The solution was heated at reflux for 1 h. Further azobisisobutyronitrile (0.10 g) was added and the mixture heated a further 3 h. The solution was concentrated in vacuo, redissolved in diethyl ether and filtered to remove insoluble succinimide. The ether solution was washed with 2 N aqueous hydrochloric acid solution followed by brine then dried over magnesium sulphate. The solution was concentrated to a volume of 150 ml then diluted with isohexane. After further partial concentration crystallization started. The mixture was allowed to stand in an ice-bath for 1 h. The resulting crystals were filtered, washed with isohexane and dried in vacuo to give the subtitled compound (17 g).

b) 5-Bromomethyl-2-chloro-N-(tricyclo[3.3.1.1$^{3,7}$]dec-1-ylmethyl)-benzamide

To a stirred solution of 5-bromomethyl-2-chloro-benzoic acid (Example 71a, 12.4 g) in dichloromethane (250 ml) and dimethylformamide (0.12 ml) at 0° C. was added oxalyl chloride (8.7 ml). The cooling bath was removed and the solution allowed to warm to room temperature. Once gas evolution had ceased the solution was concentrated in vacuo. The residue was redissolved in dichloromethane (300 ml), cooled to 0° C. and treated with diisopropylethylamine (12.4 ml) and adamantylmethylamine (7.54 ml). After 15 min, at 0° C. the solution was poured into diethyl ether (1 L) and washed with 1 N aqueous hydrochloric acid followed by brine. The organics were dried over magnesium sulphate and concentrated in vacuo to give the title compound as a white powder (19 g)

MS (APCI+ve) 396/398 (M+H)$^+$ $^1$H NMR (DMSO-d$_6$) δ 8.39 (1H, t); 7.50-7.40 (2H, m); 4.74 (2H, s); 2.92 (2H, d); 2.50 (3H, s); 1.94 (3H, s, br); 1.67 (3H, d); 1.59 (3H, d); 1.52 (6H, s).

c) 2-Chloro-5-[[(2-hydroxyethyl)amino]methyl]-N-(tricyclo[3.3.1.1$^{3,7}$]dec-1-ylmethyl)-benzamide A mixture 5-(bromomethyl)-2-chloro-N-(2-tricyclo[3.3.1.1$^{3,7}$]dec-1-ylmethyl)-benzamide (Example 71b, 0.300 g) and ethanolamine (0.5 ml) in toluene (40 ml) was heated at 100° C. for 24 h. The mixture was cooled, poured into saturated aqueous sodium hydrogencarbonate solution, extracted into ethyl acetate, dried oer magnesium sulfate, filtered and concentrated under reduced pressure to give the subtitled compound as a gum (0.280 g).

MS (APCI+ve) MW 377/379 (M+H)$^+$ d) [1-[[[[4-Chloro-3-[[(tricyclo[3.3.1.1$^{3,7}$]dec-1-ylmethyl)amino]carbonyl]phenyl]-methyl](2-hydroxyethyl)amino]methyl]cyclopropyl]-carbamic acid, 1,1-dimethylethyl ester 2-Chloro-5-[[(2-hydroxyethyl)amino]methyl]-N-(tricyclo[3.3.1.1$^{3,7}$]dec-1-ylmethyl)-benzamide (0.250 g, Example 71c), (1-formylcyclopropyl)-carbamic acid, 1,1-dimethylethyl ester (0.260 g), sodium triacetoxyborohydride (0.600 g) and dichloromethane (50 ml) were stirred together under nitrogen for 24 h. The mixture was poured into satrurated aqueous sodium hydrogencarbonate solution, extracted into dichloromethane, dried over magnesium sulfate, filtered and concentrated under reduced pressure. The crude material was purified on silica gel (ethyl acetate), to afford the subtitled compound (0.302 g).

MS (APCI+ve) MW 546/548 (M+H)+ e) 5-[[[(1-Aminocyclopropyl)methyl](2-hydroxyethyl)amino]methyl]-2-chloro-N-(tricyclo[3.3.1.1$^{3,7}$]dec-1-ylmethyl)-benzamide

[1-[[[[4-Chloro-3-[[(tricyclo[3.3.1.1$^{3,7}$]dec-1-ylmethyl)amino]carbonyl]phenyl]-methyl](2-hydroxyethyl)amino]methyl]cyclopropyl]-carbamic acid, 1,1-dimethylethyl ester (Example 71d, 0.302 g) was dissolved in methanol (10 ml) and 4 N HCl in dioxane (10 ml) was added. The mixture was stirred for 14 h at room temperature, then poured into 25% aqueous ammonia solution and concentrated under reduced pressure to give the free base. This was purified by column chromatography over silica (eluting with 19:1:0.1 dichloromethane/methanol/ammonia) to afford the title compound as an oil (0.230 g).

MS (APCI+ve) MW 446/448 (M+H)$^+$ $^1$H NMR (CDCl$_3$) δ 7.69 (1H, s); 7.37 (2H, m); 6.38 (1H, t, br); 3.73 (2H, s); 3.64 (2H, t); 3.18 (2H, d); 2.74 (2H, t); 2.49 (2H, s); 2.21 (3H, s, br); 2.01 (3H, s, br); 1.75-1.64 (6H, m); 1.59 (6H, s, br); 0.59 (2H, t); 0.40 (2H, t).

EXAMPLE 72

5-[[(2-Hydroxyethyl)[2-(methylamino)ethyl]amino]methyl]-2-methyl-N-(tricyclo[3.3.1.1$^{3,7}$]dec-1-ylmethyl)-benzamide

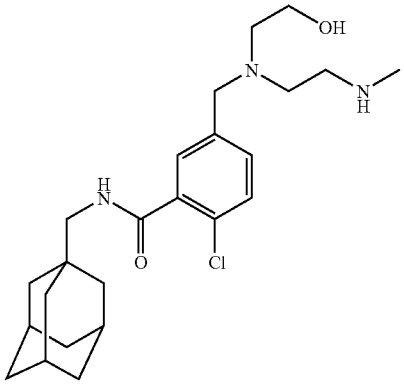

a) [2-[(2-Hydroxyethyl)[[4-methyl-3-[[(tricyclo[3.3.1.1$^{3,7}$]dec-1-ylmethyl)amino]carbonyl]phenyl]methyl]amino]ethyl]methyl-carbamic acid, 1,1-dimethylethyl ester 2-Chloro-5-[[(2-hydroxyethyl)amino]methyl]-N-(tricyclo[3.3.1.1$^{3,7}$]dec-1-ylmethyl)-benzamide (0.30 g, Example 71c), methyl(2-oxoethyl)-carbamic acid, 1,1-dimethylethyl ester (0.276 g), sodium triacetoxyborohydride (0.720 g) and dichloromethane (50 ml) were stirred together under nitrogen for 24 h. The mixture was poured into saturated aqueous sodium hydrogencarbonate solution, extracted into dichloromethane, dried over magnesium sulfate, filtered and concentrated under reduced pressure. The crude material was purified on silica (eluting with 19:1 dichloromethane/methanol) to afford the subtitled compound (0.285 g).

MS (APCI+ve) MW 534/536 (M+H)$^+$ b) 5-[[(2-Hydroxyethyl)[2-(methylamino)ethyl]amino]methyl]-2-methyl-N-(tricyclo[3.3.1.1$^{3,7}$]dec-1-ylmethyl)-benzamide

[2-[(2-Hydroxyethyl)[[4-methyl-3-[[(tricyclo[3.3.1.1$^{3,7}$]dec-1-ylmethyl)amino]carbonyl]phenyl]methyl]amino]ethyl]methyl-carbamic acid, 1,1-dimethylethyl ester (Example 72a, 0.285 g) was dissolved in methanol (10 ml), 4 N HCl in dioxane (10 ml) was added and the mixture stirred for 14 h at room temperature. The solution was poured into 25% aqueous ammonia solution and concentrated under reduced pressure to give the free base. This was purified by chromatography over silica gel (eluting with 8:2:0.2/dichloromethane:methanol:ammonia) to afford the title compound as an oil (0.167 g).

MS (APCI+ve) MW 434/436 (M+H)+

$^1$H NMR (CDCl$_3$) δ 7.65 (1H, s); 7.35 (2H, s); 6.41 (1H, t, br); 3.67 (2H, s); 3.57 (2H, t); 3.17 (2H, d); 2.68-2.61 (6H, m); 2.38 (3H, s); 2.01 (3H, s, br); 1.76-1.63 (6H, m); 1.60 (6H, s, br).

EXAMPLE 73

2-Chloro-5-[3-[[2-(1-methyl-1H-imidazol-4-yl)ethyl]amino]propyl]-N-(tricyclo[3.3.1.1$^{3,7}$]dec-1-ylmethyl)benzamide

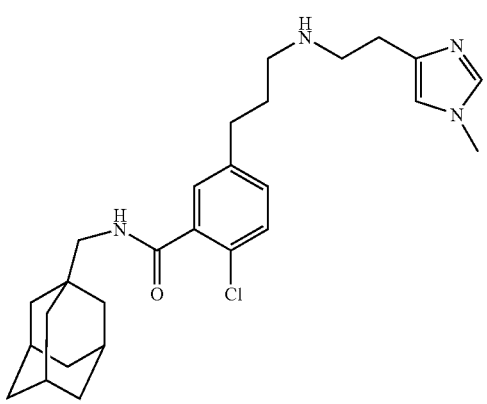

Synthesized from 2-chloro-5-[3-[(methylsulfonyl)oxy]propyl]-N-(tricyclo[3.3.1.1$^{3,7}$]dec-1-ylmethyl)-benzamide (Example 6e, 0.5 g) and 3-methylhistamine (0.22 g) according to the procedure described in Example 6f to afford the title compound (0.060 g).

MS (APCI+ve) 469/471 (M+H)$^+$ $^1$H NMR (DMSO-d$_6$) δ 9.45-9.30 (2H, m); 9.02 (1H, s); 8.32 (1H, t); 7.55 (1H, s); 7.41 (1H, d); 7.28 (1H, d); 7.26 (1H, d); 3.82 (3H, s); 3.30-3.20 (2H, m); 3.15 (2H, t); 2.95-2.85 (4H, m); 2.70 (2H, t); 2.02-1.93 (5H, m); 1.63 (6H, q); 1.52 (6H, s).

EXAMPLE 74

2-Chloro-5-[3-[[2-(1H-imidazol-4-yl)ethyl]amino]propyl]-N-(tricyclo[3.3.1.1$^{3,7}$]dec-1-ylmethyl)benzamide

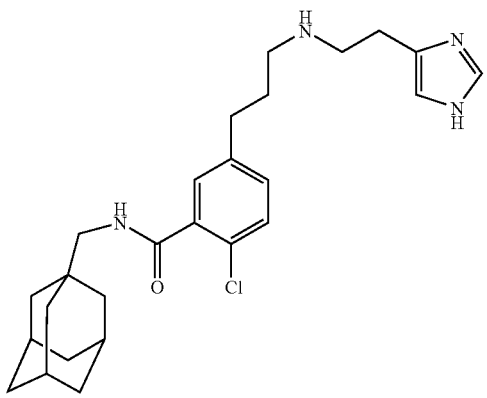

Synthesized from 2-chloro-5-[3-[(methylsulfonyl)oxy]propyl]-N-(tricyclo[3.3.1.1$^{3,7}$]dec-1-ylmethyl)-benzamide (Example 6e, 1 mg) and histamine according to the procedure described in Example 6f to afford the title compound.

MS (APCI+ve) 455/457 (M+H)$^+$

EXAMPLE 75

2-Chloro-5-[3-[[3-(1H-imidazol-1-yl)propyl]amino]propyl]-N-(tricyclo[3.3.1.1$^{3,7}$]dec-1-ylmethyl)benzamide

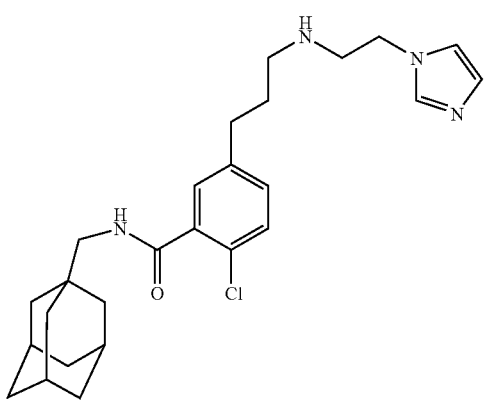

Synthesized from 2-chloro-5-[3-[(methylsulfonyl)oxy]propyl]-N-(tricyclo[3.3.1.1$^{3,7}$]dec-1-ylmethyl)-benzamide (Example 6e, 1 mg) and 1-(3-aminopropyl)imidazole according to the procedure described in Example 6f to afford the title compound.

MS (APCI+ve) 469/471 (M+H)$^+$

EXAMPLE 76

2-Chloro-5-[3-[(3-hydroxypropyl)amino]propyl]-N-(tricyclo[3.3.1.1$^{3,7}$]dec-1-ylmethyl)-benzamide, hydrochloride salt

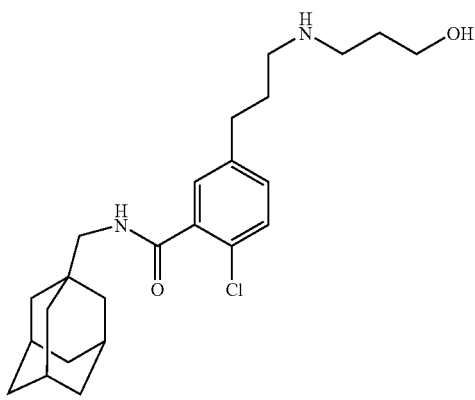

Sodium triacetoxyborohydride (4.10 g) was added to a solution of 2-chloro-5-(3-oxopropyl)-N-(tricyclo[3.3.1.1$^{3,7}$]dec-1-ylmethyl)-benzamide (3.46 g, Example 14b) and 3-aminopropanol (1.73 ml) in dichloromethane (200 ml). After 24 h the crude reaction mixture was purified by flash chromatography (eluting with 5-20% methanol/dichloromethane+1% ammonia) and the hydrochloride salt precipitated from ether/methanol 19:1, to afford the title compound as a white solid (1.60 g).

MS (APCI+ve) 419/421 (M+H)$^+$ $^1$H NMR (DMSO-d$_6$) δ 8.67 (2H, s); 8.31 (1H, t); 7.41 (1H, d); 7.30-7.25 (2H, m); 4.74 (1H, t); 3.47 (2H, q); 2.95-2.85 (6H, m); 2.67 (2H, t); 2.00-1.84 (5H, m); 1.76 (2H, quin); 1.63 (6H, q); 1.52 (6H, s).

Pharmacological Analysis

Certain compounds such as benzoylbenzoyl adenosine triphosphate (bbATP) are known to be agonists of the P2X$_7$ receptor, effecting the formation of pores in the plasma membrane (Drug Development Research (1996), 37(3), p.126). Consequently, when the receptor is activated using bbATP in the presence of ethidium bromide (a fluorescent DNA probe), an increase in the fluorescence of intercellular DNA-bound ethidium bromide is observed. The increase in fluorescence can be used as a measure of P2X$_7$ receptor activation and therefore to quantify the effect of a compound on the P2X$_7$ receptor.

In this manner, each of the title compounds of the Examples was tested for antagonist activity at the P2X$_7$ receptor. Thus, the test was performed in 96-well flat bottomed microtitre plates, the wells being filled with 250 μl of test solution comprising 200 μl of a suspension of THP-1 cells (2.5×10$^6$ cells/ml) containing 10$^{-4}$ M ethidium bromide, 25 μl of a high potassium buffer solution containing 10$^{-5}$ M bbATP, and 25 μl of the high potassium buffer solution containing 3×10$^{-5}$ M test compound. The plate was covered with a plastics sheet and incubated at 37° C. for one hour. The plate was then read in a Perkin-Elmer fluorescent plate reader, excitation 520 nm, emission 595 nm, slit widths: Ex 15 nm, Em 20 nm. For the purposes of comparison, bbATP (a P2X$_7$ receptor agonist) and pyridoxal 5-phosphate (a P2X$_7$ receptor antagonist) were used separately in the test as controls. From the readings obtained, a pIC$_{50}$ figure was calculated for each test compound, this figure being the negative logarithm of the concentration of test compound necessary to reduce the bbATP agonist activity by 50%. Each of the compounds of the Examples demonstrated antagonist activity, having a pIC$_{50}$ figure>5.0.

What is claimed is:

1. The compound 2-chloro-5-(3-oxopropyl)-N-(tricyclo[3.3.1.1$^{3,7}$]dec-1-ylmethyl)-benzamide.

* * * * *